United States Patent [19]
Ceriani et al.

[11] Patent Number: 5,972,337
[45] Date of Patent: *Oct. 26, 1999

[54] 46 KILODALTON HUMAN MILK FAT GLOBULE (HMFG) ANTIGEN, FRAGMENTS AND FUSION PROTEIN

[75] Inventors: Robeto L. Ceriani; Jerry A. Peterson, both of Lafayette; David J. Larocca, Encinitas, all of Calif.

[73] Assignee: Cancer Research Fund of Contra Costa, Walnut Creek, Calif.

[*] Notice: This patent is subject to a terminal disclaimer.

[21] Appl. No.: 08/162,402

[22] Filed: Dec. 3, 1993

Related U.S. Application Data

[63] Continuation-in-part of application No. 07/607,538, Nov. 1, 1990, Pat. No. 5,455,031.

[51] Int. Cl.⁶ .......................... A61K 39/29; A61K 39/00; C07K 2/00; C07K 1/00
[52] U.S. Cl. .................................. 424/185.1; 424/192.1; 530/300; 530/329; 530/350; 530/402
[58] Field of Search ..................... 530/350, 402, 530/300, 329; 424/185.1, 192.1

[56] References Cited

U.S. PATENT DOCUMENTS

| | | |
|---|---|---|
| 4,569,794 | 2/1986 | Smith et al. . |
| 4,879,213 | 11/1989 | Fox et al. . |
| 5,455,031 | 10/1995 | Ceriani et al. . |

OTHER PUBLICATIONS

Sheer et al. Cancer Research 48:6811–18, Dec. 1988.
Burgess et al. J. Cell Biology 111:2129–38, Nov. 1990.
Lazar et al. Mol. Cell Biology 8(3):1247–52, Mar. 1988.
Larocca, D. et al., "High level expression in *E. coli* of an alternate reading frame of pS2 mRNA that encodos a mimotope of human breast epithelial mucin tandem repeat", Hybridoma, 11(2):191–201 (1992).
Peterson, J.A. et al., "Biochemical and histological characterization of antigens preferentially expressed on the surface and cytoplasm of breast carcinoma cells identified by monoclonal antibodies against the human milk fat globule", Hybridoma, 9(3): 221–235, (1990).
Stubbs, J. D. et al., PNAS (USA), 87:84167 (1990).
Ceriani, R. L. et al., Cancer Research, 47:532 (1987).
Ceriani, R. L. et al., Somatic Cell Genetics ((4):415 (1988).
Ceriani, R. L. et al., Cancer Research, 48:4664 (1988).
Peterson, J. A. et al., Hybridoma, vol. 9(3). (1990).
Ceriani, R. L. et al., PNAS (USA) 79:5420 (1982).
Salinas, R. A. et al., Cancer Research 47:907 (1987).
Ceriani, R. L. et al., PNAS (USA), 74(2):5821 (1977).
Sasaki, M. et al., InVitro 17(2):150 (1981).
Larocca et al., "AM, 46,000 Human Milk Fat Globule Protein That is Highly Expressed in Human Breast Tumors Contains Factor VIII–like Domains[1]", *Cancer Research*, vol. 51, pp. 4994–4998 (Sep. 1991).
Ceriani et al., "A Novel Serum Assay for Breast Epithelial Antigen Using a Fusion Protein", *Analytical Biochemistry*, vol. 201, pp. 178–184 (Jan. 1992).
PCT Search Report in the corresponding PCT Application No. PCT/US94/13967 PCT/US94/13967 dated Mar. 16, 1995.

*Primary Examiner*—Anthony C. Caputa
*Assistant Examiner*—Mark Navarro
*Attorney, Agent, or Firm*—Viviana Amzel; Pretty, Schroeder & Poplawski, PC

[57] ABSTRACT

A polypeptide has the antibody binding activity of the 46 Kdalton HMFG antigen and/or homology to at least one of the light chains of clotting factors V and VIII and/or contains RGD and/or EGF-like segments. The polypeptide is provided as a recombinant and/or glycosylated and/or fusion protein. An antibody has high affinity for specificity epitopes of the polypeptide of the invention. Polynucleotide segments encode the polypeptide, recombinant and fusion protein of the invention or fragments thereof, and immunoassay kits comprise the antibodies and/or polypeptides of the invention and other components. In vivo, ex vivo, and in vitro methods of therapy, vaccination and diagnosis utilize the polypeptide, fusion protein anti-sense nucleotides, antibodies or and polynucleotides of the invention.

22 Claims, 2 Drawing Sheets

46 KILODALTON HUMAN MILK FAT GLOBULE (HMFG) ANTIGEN, FRAGMENTS AND FUSION PROTEIN

This application is a continuation-in-part of U.S. patent application Ser. No. 07/607,538 filed Nov. 1, 1990, now U.S. Pat. No. 5,455,031.

BACKGROUND OF THE INVENTION

1. Field of the Invention

This invention relates to the field of diagnosis and therapy of cancer and the prevention and treatment of viral infections. More particularly, it relates to a polypeptide having the antibody binding specificity of the 46 Kdalton HMFG antigen, hybrid protein thereof, anti-idiotype antibodies and polynucleotides, anti-sense polynucleotides encoding them, kits, and their application to the in vitro detection, the in vivo and ex vivo of delivery of a therapeutic agent, the detection of the polynucleotides by hybridization with labeled probes, and the vaccination against and treatment of cancer and viral infections.

2. Description of the Background

The human milk fat globule (HMFG) has been used extensively as a source of antigenic material for the preparation of both polyclonal and monoclonal antibodies that have found widespread use in the diagnosis of breast cancer, as well as in the study of the breast epithelial cell surface and the processing of its antigenic components.

Polyclonal antiserum was originally prepared, that after appropriate absorptions with non-breast tissue was found to identify surface antigens of human mammary epithelial cells (HME-Ags). This antiserum (anti-HME) had a high specificity for normal breast epithelial cells and breast carcinomas. It identified mainly three components of the human milk fat globule which had molecular weights of 150 Kdalton, 70 Kdalton, and 46 Kdalton, respectively.

Monoclonal antibodies were first made against the HMFG in 1980. These antibodies were applied to identify a hitherto unknown component of the breast epithelial cell surface, a large molecular weight mucin-like glycoprotein, that was named non-penetrating glycoprotein (NPGP). This latter component appears to be extremely antigenic in the mouse. The vast majority of monoclonal antibodies prepared against HMFG as well as breast tumors have been found to have specificity against different epitopes of this mucin. Less frequently, monoclonal antibodies have been prepared against the 70 Kdalton and 46 Kdalton components of the HMFG.

The reason for the high immunogenicity of NPGP was elucidated by the characterization of cDNA clones selected from a λgt11 breast cell library using both polyclonal and monoclonal antibodies against the mucin. These cDNA clones consist of large arrays of highly conserved 60 bp tandem repeats. The resulting 20 amino acid repeat contains epitopes for several anti-mucin antibodies. The repeat is apparently unstable at the genomic level. This may account for the observed polymorphism seen at the gene, RNA and protein levels for this high molecular weight mucin. An initial report on cDNA cloning of the mucin product suggested that the core protein had a molecular weight of about 68 Kdalton. However, the mRNA was found to be large enough to code for proteins from about 170 Kdalton to 230 Kdalton. More recently, using milder deglycosylation methods, a core protein was identified having a molecular weight of about 200 Kdalton. Attention has also been devoted to the study and use of the NPGP mucin, largely as a result of its high immunogenicity. Thus, a large number of monoclonal antibodies were prepared against it. However, the smaller components of HMFG also appear to be important molecules on the surface of breast epithelial cells. They have a breast specificity as demonstrated by the anti-HMFG antibodies.

The 46 Kdalton and 70 Kdalton HMFG antigens are found in serum of breast cancer patients and thus can be used as markers for breast cancer in serum assays. In addition, the 70 Kdalton component has been found to co-purify with the intact mucin complex and has been reported to be associated with the NPGP mucin complex by means of disulfide bonds, making it a possible linker protein of this surface mucin complex. Polyclonal antibodies against a major component of the HMFG having molecular weight of 155 Kdaltons have been prepared. It was found that antisera bound also to the apical surface of lobules and terminal ducts, but not to the larger ducts of the mammary gland. The latter also did not bind to the apical surface of normal apocrine and eccrine sweat gland coils and ducts, or sebaceous glands in skin. The MFGM-gp155 did become localized in Paget's disease and breast disease but not in cases of extramammary disease.

Few monoclonal antibodies, however, have been prepared against the smaller components of the HMFG system, such as the 70 Kdalton and 46 Kdalton HMFG antigens. The breast mucin glycoprotein molecule appears to be highly antigenic because of its internally repeated structure. The components of the mucin glycoprotein was recently determined and a partial sequence for the 70 Kdalton antigen obtained by cDNA cloning. A role for the 70 Kdalton antigen has been suggested as a linker protein for the breast mucin. The 46 Kdalton component of the HMFG system has been found to be present in the serum of breast cancer patients. In addition, with the aid of both monoclonal and polyclonal antibodies against the 46 Kdalton HMFG antigen, circulating immune complexes of the 46 Kdalton HMFG antigen were detected in breast cancer patients, and an increase in the circulating 46 Kdalton HMFG antigen was found to be associated with tumor burden.

Accordingly, there is still a need for an improved product and methods suitable for diagnostic and therapeutic applications to human cancer and virus-associated infections.

SUMMARY OF THE INVENTION

This invention relates to a pure, isolated polypeptide having the antibody binding specificity of the 46 Kdalton HMFG antigen and/or homology to at least a portion of a light chain of clotting factors V and VIII, and/or RGD and/or EGF-like segments, and to a composition comprising the polypeptide and a biologically acceptable carrier, e.g. a pharmaceutically-acceptable carrier. The naked polypeptide may be produced by recombinant cloning and expression in prokaryotes and the glycosylated version in eukaryotes. The polypeptide of the invention is also provided, with a second antigenic polypeptide bound thereto, as a fusion protein and as a composition comprising the hybrid protein and a biologically acceptable carrier, e.g. a pharmaceutically-acceptable carrier. An antibody detecting kit provided comprises, in separate containers, the polypeptide of the invention or a functional fragment thereof, anti-constant region immunoglobulin or protein G or A or fragments thereof, and instructions for its use. Another kit comprises, in separate containers, the fusion protein of the invention comprising a second antigenic polypeptide, or an anti-second polypeptide polyclonal or monoclonal antibody, and anti-constant region immunoglobulin, protein G or A or binding fragments thereof. The polypeptide of this invention or a binding fragment thereof may also be applied to the vaccination of a mammal such as a human in an amount and under conditions effective to raise antibodies which are capable of selectively binding to the 46 Kdalton HMFG antigen, functional fragments, or cells carrying them. Yet another application for the polypeptide of the invention is in the in vitro detection of circulating anti-46 Kdalton HMFG antigen antibody. This can be attained by adding the polypeptide of the invention or a functional fragment thereof to a sample under conditions effective to form an antibody-polypeptide complex, and determining the presence of any complex formed. The polypeptide of this invention or a functional fragment thereof is also useful for the therapeutic treatment of viral infections such as those associated with the HIV and rotavirus, among others. This may be attained by, e.g. feeding a subject the polypeptide of the invention or a functional fragment thereof in an amount and under conditions effective to treat or prevent the viral infection. The polypeptide may be utilized as such or in glycosylated form. Another way of detecting the presence of circulating anti-46 Kdalton HMFG antigen antibody is by contacting a sample with the fusion protein of this invention to form an antibody-fusion protein complex, then adding an anti-second polypeptide antibody to form a double antibody-fusion protein complex, and determining the presence of any double antibody complex formed. The assay may be a solid-phase assay, e.g. where the fusion protein is attached to a solid support.

Still part of this invention are antibodies having high selectivity, affinity and specificity for the 46 Kdalton HMFG antigen, and as anti-idiotype antibodies, and to a composition comprising the antibodies and a biologically acceptable carrier, e.g. a pharmaceutically-acceptable carrier. The antibodies are also provided as an immunoassay kit that comprises, in addition, in separate containers, the monoclonal antibody having high affinity, selectivity and specificity for the 46 Kdalton HMFG antigen or a functional fragment thereof, an anti-constant region immunoglobulin or protein G or A or fragments thereof, and instructions for its use. Also encompassed by this invention is an anti-cancer kit comprising, in separate containers, a monoclonal antibody having specificity for the 46 Kdalton HMFG antigen, and an anti-cancer therapeutic agent selected from the group consisting of immunotoxins and radionucleides, among others. The antibodies selectively binding the 46 Kdalton HMFG antigen are useful for detecting the presence of cancer cells, the polypeptide or fragments thereof in a biological sample such as milk, serum and the like. They may be added to a biological sample of cancerous origin to form an antibody-polypeptide complex, and then determining the presence of any complex formed. The antibodies may also be applied to determining the presence of circulating epithelial cells in a biological sample by adding them to the sample under conditions effective to form an antibody-cell polypeptide complex, and determining the presence of any complex formed. Cells that express the polypeptide of the invention or fragments thereof may be imaged by administering to a subject suspected of being afflicted with cancer or under cancer therapy the anti-46 Kdalton antibody of the invention under conditions effective to deliver it to target body cells expressing the 46 Kdalton HMFG antigen or fragments thereof to form an antibody-cellular antigen complex, then administering to the subject a detectable labeled molecule capable of binding to the antibody at a site other than its binding site for the cellular antigen, and non-invasively detecting the presence of label in the subject's body associated with any complex formed.

This invention also relates to polynucleotides encoding the polypeptide described herein or antibody binding fragments thereof as well as polynucleotides encoding the fusion protein of the invention or antibody binding fragments thereof, DNA segments which are complementary to the polynucleotides provided herein, and hybrid polynucleotides, hybrid vectors and host cells transfected with the vectors. The DNA and RNA segments of the invention may be used for the production of the polypeptides and in a method of detecting the presence of a polynucleotide segment encoding the polypeptide described above or fragments thereof by hybridization under pre-set conditions. A group of polynucleotides comprising an anti-sense segment to a polynucleotide encoding the polypeptide of the invention or antibody binding fragments thereof of about 15 to 3000 bases. These polynucleotides are suitable for treating breast cancer by their administration to a patient therapeutic amount. A therapeutic agent may be delivered in vivo to target cells expressing the 46 Kdalton HMFG antigen antigen or fragments thereof to form an antibody-cellular antigen complex, then administering to the subject a detectable labeled molecule capable of binding to the antibody at a site other than its binding site for the cellular antigen, and non-invasively detecting the presence of label in the subject's body associated with any complex formed.

This invention also relates to polynucleotides encoding the polypeptide described herein or antibody binding fragments thereof as well as polynucleotides encoding the fusion protein of the invention or antibody binding fragments thereof, DNA segments which are complementary to the polynucleotides provided herein, and hybrid polynucleotides, hybrid vectors and host cells transfected with the vectors. The DNA and RNA segments of the invention may be used for the production of the polypeptides and in a method of detecting the presence of a polynucleotide segment encoding the polypeptide described above or fragments thereof by hybridization under pre-set conditions. A group of polynucleotides comprising an anti-sense segment to a polynucleotide encoding the polypeptide of the invention or antibody binding fragments thereof of about 15 to 3000 bases. These polynucleotides are suitable for treating breast cancer by their administration to a patient therapeutic amount. A therapeutic agent may be delivered in vivo to target cells expressing the 46 Kdalton HMFG antigen or a functional fragment thereof by administering it to a subject suspected of carrying target cells, such as malignant tumor cells, in a therapeutic amount operatively linked to the anti-46 Kdalton HMFG antigen antibody at a site other than the antigen's binding site under conditions effective for reaching the target cells environment, and allowing the antibody to bind to the cells and the therapeutic agent to act upon the cells. A therapeutic agent may also be delivered ex vivo to target cells expressing the 46 Kdalton HMFG antigen or a functional fragment thereof by, contacting the anti-46 Kdalton HMFG antigen antibody carrying the therapeutic agent with a sample containing the target cells, such as cancer cells under conditions effective to promote the formation of antibody-cell polypeptide complexes, separating any complexes formed, and returning the sample to the subject.

A more complete appreciation of the invention and many of the intended advantages thereof will be readily perceived as the same becomes better understood by reference to the following detailed description when considered in connection with the accompanying figures.

Figure 1:
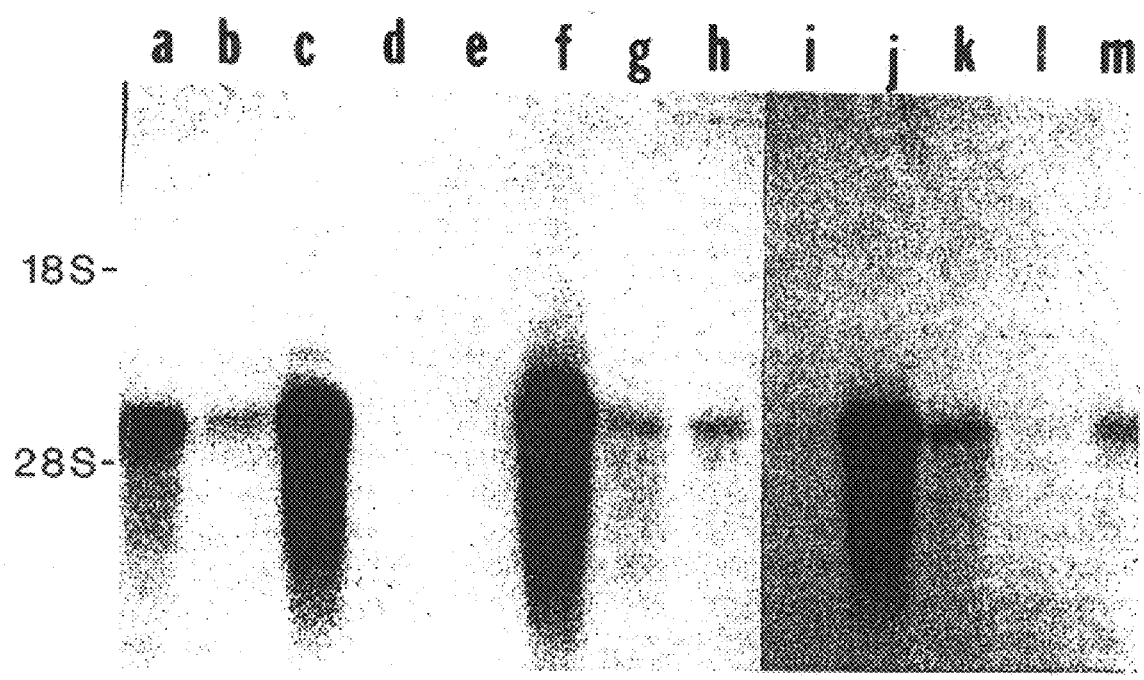
FIG. 1 shows the expression of BA46-1 specific mRNA in human carcinoma cell lines. Total RNA (20 ug/lane) was run on a 1.4% agarose gel, blotted, and hybridized to $^{32}$P labelled RNA generated from the BA46-1 cDNA clone. The contents of the samples in the different lanes are as follows: a) A549 (lung); b) BT20 (breast); c) ELLG (breast); d) Raji (lymphoid); e) SKBR3 (breast); f) SKOV3 (ovary); g) MDA-MB-361 (breast); h) MDA-MB-331 (breast) i) HeLa (cervix); j) HS578T (breast); k) HT29 (colon); l) PanCl (pancreas); m) MCF7 (breast). Exposure was 16 hours with an intensifying screen.

Other objects, advantages and features of the present invention will become apparent to those skilled in the art from the following discussion.

BEST MODE FOR CARRYING OUT THE INVENTION

This invention arose from a desire by the inventors to improve on technology useful for the detection, diagnosis, and treatment of breast cancer of epithelial origin and/or prevent viral infections. Monoclonal antibodies against the 46 Kdalton HMFG antigen have also shown some effectiveness in the radioimmunotherapy of transplanted human breast tumors in experimental animals nude mice. Moreover, an impure preparation of the 46 Kdalton HMFG antigen also been implicated in the inhibition of viruses, such as rotaviruses which are infectious agents causing gastroenteritis, particularly affecting infants, young children and immunologically compromised patients. This work relies on the isolation of cDNA clones that encode partial DNA sequences of the 46 Kdalton apparent molecular weight (app. MW) polypeptide component of the HMFG system and of monoclonal antibodies that bind the 46 Kdalton component of the human milkd fat globule (HMFG) system with high affinity and selectivity. The HMFG membrane system, in fact, truly represents a purified portion of the apical surface of the normal breast epithelial cell. The 46 Kdalton app. MW component is a major molecular species of the HMFG membrane and represents a major and important component of the apical surface of the normal breast epithelial cell. Nucleotide and deduced amino acid sequences of a partial cDNA fragment obtained first are shown in Table 1 of Example 7 below. The partial amino acid sequence of the encoded polypeptide is about 217 amino acids long, has a theoretical MW of about 25 Kdaltons and represents the C-terminus of the 46 Kdalton HMFG antigen. This fragment contain four potential sites for N-linked glycosylation and is asparagine and leucine rich. Starting from the C-terminus, the nucleotide sequence extends to the 3' end of the mRNA which contains the AATATA consensus sequence preceding the poly-A segment for cleavage and polyadenylation. A comparison of the C-terminal nucleotide sequence to sequences in the EMBL database using FSTNSCAN (PCGENE) revealed extensive homology with human serum factors V and VIII, and with protein C. The C-terminal deduced protein sequence, however, shares identity only with factors V and VIII but not with protein C since the homology at the nucleotide level is found in an intervening sequence (See, Table 2 below). There is also an about 43% identity to factor V and about 38% identity to factor VIII. The regions of factors V and VIII shown in Table 2 share an about 47% identity with the fragment of the protein shown. The results of the analysis of the deduced amino acid sequence of the C-terminal 46 Kdalton antigen fragment are consistent with it being a glycosylated protein. Its homology to clotting factors V and VIII may be found in the C1C2 region of the light chain of factor VIII. Human antibodies that bind this region of the light chain of factor VIII inhibit the factor by preventing its interaction with phospholipids, and since this region of factor VIII has been implicated in phospholipid binding, it is likely that the homologous region in the C-terminus of the 46 molecular weight HMFG polypeptide serves a similar role. The appearance of a shared domain in otherwise different proteins may be due to exon shuffling. The C-terminus of the 46 Kdalton HMFG angiten may serve as a novel "anchor" sequence for the 46 Kdalton HMFG protein or it may be involved in the binding of mucin and/or cell membranes to the phospholipids found on the surface of growing milk fat droplets. Alternatively, the homologous sequence may be involved in the assembly of the mucin complex at the plasma membrane surface.

The single stranded RNA probe provided herein is complementary to the ORF found in the cDNA insert, that is in frame with the β-galactosidase DNA sequence in the λgt11 vector. This ORF, therefore, represents the sense strand of the C-terminal portion of the gene since only the complementary strand probe binds to a specific 2.2 kilobase mRNA of epithelial cell lines. The cDNA sequence encoding the C-terminus of the 46 Kdalton HMFG glycoprotein was reported in the original text of this patent, and its deduced amino acid sequence showed to have extensive sequence similarity with the C1C2 domain of human coagulation factors V and VIII (43% and 38% respectively). Upon further searching, other proteins were found that have sequences similar to the C1C2 domain of factors V and VIII. These include a neuronal recognition molecule (A5 antigen) of Xenopus (Takagi et al, Neuron 7:295 (1991)), discoidin I of Dictyostelium discoideum (Poole et al, PNAS (USA) 90:5677 (1993)), a receptor tyrosine kinase with an extracellular discoidin I-like domain (Johnson et al, PNAS (USA) 90:5677 (1993)), a 63/55 molecular weight glycoprotein of the mouse milk fat globule (Stubbs et al, PNAS (USA) 87:8417 (1990)), and components 15/16 and GP55 of bovine and guinea-pig milk fat globule (Mather et al, Biochem. Mol. Biol. Int. 29:545 (1 993)), respectively. Homologous portion of their sequences are shown in Table 6 below. When the complete gene was sequenced, it was found that the largest open reading frame of the BA46 cDNA clone encodes a protein of about 387 amino acids with an estimated molecular weight of about 43,123 Kdaltons. The actual correspondence of the cDNA cloned to the 46 Kdalton HMFG glycoprotein antigen isolated from the HMFG is shown by correlating the levels of mRNA with that of the expressed the 46 Kdalton HMFG antigen in different breast cell lines, and the binding of the monoclonal antibodies used in the cDNA screening to the pEX/LB21 fusion protein expressed in E. coli. In addition, five defined and distinct epitopes in the C-terminal end of the protein were determined by epitope mapping for two monoclonal antibodies of the cocktail used in the original screening of the cDNA library (Mc8=DPRTG, and Mc16=SSKIF) (See, Table 4 below). The two other monoclonal antibodies (Mc3, Mc15) neither bound to the fusion protein nor to any of the peptide hexamers used in the epitope mapping of the C-terminal region (amino acids 330–382) of the 46 Kdalton polypeptide. However, the two monoclonal antibodies, Mc3 and Mc15, bound to the full length recombinant polypeptide produced by expression in bacteria of the complete cloned cDNA sequence encompassing the entire ORF but not the signal peptide.

The amino acid sequence of the polypeptide deduced with the help of the PC/GENE DNA and the protein analysis programs (IntelliGenetics, Inc.) revealed the existence of homologies or sequence similarities with several functional domains. At the N-terminal end of the polypeptide, there is a hydrophobic region positioned after the Met start codon which most likely corresponds to a signal peptide. Cleavage most likely occurs between $Val_{21}$ and $Ala_{22}$, leaving a cleaved peptide of 21 amino acids plus the methionine. This cleavage results in a processed polypeptide of about 40,862 Kdaltons. Amino acids 46 to 48, RGD, represent a known cell adhesion sequence, and following this is an EGF-like domain of approximately 12 amino acids encompassing amino acids 55 to 66. The C-terminal end of the polypeptide starting at amino acid 69, comprises a domain with homology to the C1C2 region of human coagulation factors V and VIII, a portion of which is shown in Table 1 below. This sequence contains four potential N-linked glycosylation sites, all present in the C1C2-like domain, numerous potential O-linked glycosylation sites, disulfide linkages, and phosphorylation sites (e.g. protein kinase C and casein kinase II sites). The greatest homology, however, is seen with the 66/55 Kdalton antigen MFGE8 isolated from the mouse milk fat globule (Stubbs et al., supra). These results permit the grouping of the 46 Kdalton HMFG polypeptide with growth factors and other molecules associated with cell adhesion interactions, e.g. associated with breast epithelial cells, that provide a possible autocrine/paracrine function. The 46 Kdalton HMFG antigen thus is likely a selectin-like molecule, which has the general structure of an N-terminal adhesion domain (lectin domain) followed by an EGF-like domain, a variable number of complement regulatory elements, a membrane-association domain (a single transmembrane sequence), and a short cytoplasmic tail. Although the 46-Kdalton antigen appears to lack a trans-membrane domain, the C-type domain is very likely the means by which the 46 Kdalton HMFG antigen associates with the cell membrane by interaction with phospholipids. The possible cell interaction properties may be mediated via the cell adhesion sequence RGD since breast cells are known to possess integrins that have receptors for this sequence. The auto-crine/paracrine properties may be mediated by the EGF-like sequence. The 46 Kdalton HMFG polypeptide is abundantly present in the HMFG and the expression of its mouse homologue is increased during lactation. Thus, the expression of the human 46 Kdalton HMFG and its mouse homologue are associated with differentiation in the breast. The production of the molecules is highly increased during lactation. Thus, except for periods of lactation, only cancer cells will express high amount of the 46 Kdalton HMFG antigen. Normal resting breast cells do not stain with anti-46 Kdalton HMFG antigen antibodies, showing the antigen to be substantially absent under these conditions.

Although the antibodies used to select the cDNA were specific to the Kdalton HMFG antigen, and happened to bind to breast carcinomas, the expression of the 2.2 kb mRNA that encodes the 46 Kdalton protein occurs in other cancer cell lines. The broad specificity found for cancers from tissues of different origins is attributable to a deregulation of this gene in neoplastic tumors such as carcinomas but not in normal tissue. Although the 46 Kdalton app. MW HMFG antigen may also be expressed by normal epithelial tissue cells, although at a lower level, it is processed in a way that blocks the epitopes that are exposed in the breast cell version of the polypeptide by, for example, producing alterations in its glycosylation. The HMFG mucin is also expressed in non-breast cancer cells such as non-breast carcinoma cells, but its altered processing in the pancreas, for example, leads to the exposure of different antigenic sites than in the breast.

The fusion protein is useful for assaying the presence of the 46 Kdalton HMFG antigen or fragments thereof in sera obtained from cancer patients, such as patients suffering from breast carcinomas and also in milk of nursing mothers, among others. This fusion protein is also useful as an immunogen for generating second generation monoclonal and polyclonal antibodies of increased affinity for the antigen. These antibodies may be used, among other applications, to further study the tissue distribution of this antigen and its involvement in the synthesis of its messenger RNA in improved immunoassays, and in the therapy of cancers of epithelial origin, both in vivo and ex vivo.

Many monoclonal antibodies raised against the C-terminus or the complete 46 Kdalton HMFG antigen serve to detect the respective epitopes present on this molecule by radioimmunobinding on HMFG membranes, whole milk, milk fractions, and on cancerous membrane material, such as those obtained from breast cancer patients. These monoclonal antibodies do not stain either normal breast tissue nor any other normal tissue when tested by immunohistology. Since some breast carcinomas have very high levels of mRNA encoding the 46 Kdalton HMFG antigenic component, it is possible that second generation antibodies, both monoclonal and polyclonal made against the fusion protein have different, and possibly improved, specificity for detecting the 46 Kdalton HMFG antigenic component by immunohistopathology.

Northern blots using the cDNA clone in the present work showed that the HMFG 46 Kdalton mRNA is present in most breast carcinoma cell lines tested, and in several non-breast carcinoma cell lines, and was still present but at lower levels in one lymphoid cell line (Raji). However, the expression levels of the 2.2 kbase RNA encoding the 46 Kdalton HMFG antigen detected vary considerably even amongst carcinoma cell lines. Carcinoma cell lines such as those from lung cells (A549), ovary cells (SKOV3) and two breast cell lines (Ell-G and HS578T) accumulated much more of the RNA transcript than other carcinoma cell lines. In other cases, such as in that of Her 2/neu, and the EGF-like receptor in breast and other carcinomas, the overexpression of certain genes has been correlated with prognosis of the disease. The overexpression of the 46 Kdalton HMFG antigen in neoplastic cells such as carcinoma cellsl in thus correlatable with the development of cancer disease. Clearly, the 46 Kdalton HMFG antigen was shown herein to evidence epithelial specificity. However, certain epitopes of the 46 Kdalton HMFG antigen may have broader specificity for types of breast cells other than epithelial cells. The 46 Kdalton HMFG polypeptide is expressed significantly in malignant cells such as carcinoma cells due to the deregulation of expression associated with malignancy. The 46 Kdalton HMFG antigen mRNA is highly expressed in cancer cells such as carcinoma cells of breast and other origins. This is in contrast to its absence, in a form that is immunologically recognizable, from the corresponding normal cells.

Having cloned a portion of the cDNA of this molecule permitted the further deduction of the sequence of the encoded polypeptide C-terminus. It also permitted the pursuit of further clones leading to the synthesis of recombinant DNA segments, polypeptides and fusion proteins containing the partial, and ultimately the complete 46 Kdalton amino acid sequence and fragments thereof as well as the preparation of a new generation of monoclonal antibodies against specific epitopes of this polypeptide. The hybrid DNA and fusion protein of the invention permitted the preparation of polyclonal and monoclonal antibodies against the fusion protein of even greater specificity and/or affinity for any particular type of tissue, such as neoplastic cells of a specific organ or cancer type origin. The various cDNA clones obtained after the sequencing of the C-terminus allowed the deduction of the amino acid sequence of the 46 Kdalton app. MW HMFG antigen component of the HMFG system but the original work led solely to a segment of slightly over 800 bases (217 amino acids) long before the appearance of an EcoR1 restriction enzyme site sequence, unbeknownst to the inventors, precluded its extension. The remaining portion, representing its N-terminus, would only be arrived at after a lengthy procedural path and trying numerous different methods.

The cDNA clones encoding the C-terminal 46 Kdalton HMFG antigen fragment were isolated by screening breast cell λgt11 cDNA libraries using antibodies against the 46 Kdalton MW HMFG antigen. These libraries were made, as are most other cDNA libraries, by isolating mRNA from the breast cells, preparing cDNA using poly-dT primers or random primers and a reverse transcriptase enzyme, cutting with the restriction enzyme EcoRI, and cloning into the λgt11 expression vector at the EcoRI restriction site. The hybrid λgt11 phages were then used to infect a susceptible bacterial strain, and when plaques developed on the bacterial lawn spread on petri dishes, the plaques were blotted onto a nitrocellulose membrane, the membranes incubated with anti-46 Kdalton MW HMFG antigen antibodies and the plaques that bound the antibody were visualized by exposure to a photographic plate using a radioactively labeled second antibody against the first antibody. Positive plaques were then picked and their cDNA inserts isolated and sequenced. Although proven successful in obtaining cDNA fragments encoding the C-terminus of the 46 Kdalton MW HMFG antigen, even after many attempts this method did not facilitate the extension of the DNA sequence in the 5' direction beyond the specific point shown in Table 1 below (the EcoR1 site). As it was learned much later, after a long road plagued by unsuccessful cul-de-sacs, the major reason for the difficulties encountered in obtaining a full length DNA piece was the presence of an EcoR1 restriction site at the specific site of the cDNA encoding the 46 Kdalton MW HMFG antigen represented by the 5' end of the C-terminal fragment isolated initially. The difficulties encountered which precluded extending the DNA synthesis beyond this EcoRI site are inherent to the manner in which such cDNA libraries are made, and where the DNA fragments are cut and inserted into the λgt11 vector: at an EcoRI site. Thus, the 46 Kdalton MW HMFG antigen cDNA fragments in this library encompassed sequences towards the 5' direction to this EcoRI site that were not obtaineable with available antibodies recognizing mostly protein epitopes encoded by regions located 3' to this EcoRI site. The antibodies utilized herein are the sole antibodies ever made by anyone against the 46 Kdalton HMFG antigen. Therefore, very few, if any, of the 46 Kdalton MW HMFG antigen cDNA clones could be extended beyond this EcoRI site. In addition, another consequence of the manner in which cDNA fragments are cloned into a phage is a low probability (1 in 6) or a 1:6 proportion of cDNAs cloned in the right direction. When antibodies are used for screening a cDNA library, their effectiveness is reduced because only 1 out of 6 cDNA inserts in the library will be found to be in the right orientation and proper reading frame to code for the correct protein sequence. Therefore, the abundance of inserts containing sequences 5' to the EcoRI site in the 46 Kdalton MW HMFG antigen cDNA in these cDNA libraries was much too low to allow their detection and/or isolation.

In addition to the above, another method of screening the hybrid phage library was also tried. In this method, the libraries were screened with radiolabeled 46 Kdalton MW HMFG antigen cDNAs which, regardless of their orientation or reading frame, would bind to all inserts, but even here the desired sequences were present in amounts too low to be detected and consequently did not lead to obtaining DNA segments extending beyond this site. Still another method was utilized, the rapid amplification of cDNA ends (RACE) method to attempt to overcome the stumbling block encountered (Frohman, M. A. et al., PNAS (USA) 85:8998–9002, (1988)). The RACE protocol generates cDNA fragments by PCR amplification of regions located between a single point in the transcript and either the 3' or the 5' end of the molecule. This is attained with the use of primers specially tailored to these two end regions. As the RACE method was applied herein, a short stretch of the target cDNA segment had to be known. Primers oriented in the 3' and 5' directions were designed, which provided specificity to the amplification step starting from this region. The extension of the transcribed cDNA fragment starting from the ends of the mRNA was acomplished with primers that annealed to the natural 3' end or to an added synthetic 5' end polyA tail. The isolation of the 5' end was attained by means of reverse transcription with a gene-specific primer. The polyA homopolymer was then appended to the 5' end of the fragment with the help of terminal transferases. This added a polyA tail to the single stranded cDNA reaction product. The final amplification was accomplished using a hybrid primer, [oligo-dT of 17 residues linked to a unique 17 base oligonucleotide ("adaptor") primer], and a second gene-specific primer upstream of the first one. The amplified sequence was then cloned and sequenced. Although successful for obtaining some clones of the 3' end, the RACE protocol, even though repeated numerous times, proved unsuccessful to complete the sequence of the cDNA encoding the 5' end of the 46 Kdalton MW HMFG antigen. In this case, the lack of success stemmed from the unexpected occurrence of a secondary structure in the 5' end of the 46 Kdalton MW HMFG antigen mRNA and an inadequate polyA tailing.

Another method involving the use of PCR technology utilized the direct amplification of cloned cDNAs encoding the 5' end of the 46 Kdalton MW HMFG antigen from a breast cell λgt11 cDNA library. Utilized as primers in this case were a downstream primer close to the 5' end of the cDNA encoding the known partial 46 Kdalton MW HMFG antigen and an upstream primer in the λgt11 phage sequence. These two primers did help amplify inserts containing stretches of the unknown 5' sequences. In this manner, ten amplified cDNAs were isolated, cloned and sequenced. Disappointingly, however, this proved to be another blind alley since all these clones had significantly different sequences. Some of these cDNAs appeared to extend the DNA fragment encoding the 46 Kdalton MW HMFG antigen beyond the impervious EcoRI restriction site, thus confirming its existence which had only been presumed up to this point from the earlier attempts with antibody screening of the λgt11 cDNA library, but then all the DNA sequences thus obtained diverged. These spurious results were probably due to mispriming and amplification of other DNA sequences in the process.

An improvement on the RACE method was then implemented that, instead of using polyA tailing, used an AmpliFINDER anchor attached by ligation to the 5' end of a single stranded cDNA synthesized by reverse transcription of breast cell mRNA. Another improvement added to the protocol was the use of a heat-stable reverse transcriptase that is active at 52° C. (conventional reverse transcriptases require 42° C.). The higher temperature was used to overcome a previous problem by reducing any secondary structure that might prevent the transcription of the mRNA by the reverse transcriptase enzyme. The AmpliFINDER anchor was attached to the 5' end and used as a site for priming the PCR amplification of sequences between the 5' end and the site of the second primer in the known sequence of the cDNA encoding the 46 Kdalton MW HMFG antigen. The complete DNA sequence of the 46 Kdalton HMFG MW antigen was obtained with this AmpliFINDER RACE protocol and matched with the correct sequence out of the ten sequences obtained from the cDNA library by the PCR amplification method utilized earlier. Thus, the authentic DNA sequence of the unknown portion of the ORF encoding the 46 Kdalton HMFG antigen without the 5' non-coding region was finally obtained.

This clearly illustrates the difficulties encountered and the unexpected and unobvious path travelled to obtain the complete sequence of the cDNA encoding the 46 Kdalton MW HMFG antigen, and the deduced amino acid sequence of the product.

The cDNA clones obtained also allowed the preparation of a new generation of monoclonal antibodies that have sufficient specificity for application to cancer immunotherapy, sufficient staining ability for doing immunohistopathology, greater ability for prognosis, diagnosis, imaging and therapy, and that can better identify the 46 Kdalton HMFG peptide and fragments thereof in the sera of cancer patients and milk of pregnant females and viral-infected patients, among others. The latter property makes these antibodies useful in the diagnosis of cancer and viral infection, and for the screening and early detection of the disease in humans.

This invention thus provides a polypeptide having the antibody binding selectivity and specificity of the 46 Kdalton MW HMFG antigen and/or homology to at least one of the light chains of clotting factors V and VIII and/or comprising a RGD and/or EGF-like segment. In one preferred embodiment, the polypeptide has the biological activity of the 46 Kdalton MW HMFG antigen, and more preferably the polypeptide comprises the 46 Kdalton MW HMFG antigen itself or an antibody binding fragment thereof. The polypeptide or fragments thereof may be prepared by recombinant methods, which permit the arbitrary determination of its length and modification to be introduced at the DNA level. The polypeptide of the invention may be about 5 to 1,500 amino acids long, 90 to 500 amino acids long, more preferably about 110 to 280 amino acids long, and still more preferably about 200 to 250 amino acids long. In another preferred embodiment, the polypeptide has the amino acid sequence shown in Table 4 (SEQ. ID No: 6) or that shown in Table 2 (SEQ. ID No: 3) or antibody binding fragments thereof, preferably about 5 to 100 amino acids long, and more preferably about 15 to 50 amino acids long. Particularly preferred are polypeptide fragments which correspond to the specific epitopes which are recognized by the anti-46 Kdalton MW HMFG antigen antibodies prepared in accordance with this invention and those containing the RGD and EGF-like segments. The non-glycosylated and glycosylated polypeptide of the invention may be synthetically prepared by methods known in the art such as chemical synthesis and the like. In addition, it may be produced as a non-glycosylated product in bacteria or in glycosylated form in plants or eukaryotic cells or hosts by recloning in appropriate expression vectors and transfection of receptive hosts.

The polypeptide of the invention also has anti-viral properties. Upon fractionation of the human milk fat globules, human milk globule membrane which is the globule's macromolecular component, and its acidic protein fraction retain the anti-viral activity. When the defatted milk fat globule fraction is separated into different fractions, the anti-viral activity of human milk remains mostly with the mucin complex. However, when the mucin complex is separated into its components the highest anti-viral activity is found with 46 Kdalton app. MW HMFG antigen. The 46 Kdalton app. MW HMFG antigen preferentially binds, e.g. simian and human rotaviruses when compared to the 70 Kdalton app. MW HMFG antigen and the 46 Kdalton MW HMFG antigen depleted milk mucin. The human milk fat globules, the macromolecular fraction and the milk mucin complex, which among other fractions contains the 46 Kdalton app. MW HMFG antigen, and the 46 Kdalton app. MW HMFG antigen were all found to inhibit viral infection, e.g., by rotavirus of human and simian origin, of cultured mammalian cells. The mucin complex was shown to inhibit viral infection with a 3000 fold greater specific activity than whole milk. These results are unexpected based on previous ambiguous reports relating to the effect of human milk on rotavirus, and the reported inhibitory effects of other milk components on this virus. The human 46 Kdalton app. MW HMFG antigen was also shown to bind to cells and cell extracts that are infected with human viruses such as rotavirus. Human strains of the virus, such as RRV, Wa, DS-1, P and ST-3, bind to the 46 Kdalton app. MW HMFG antigen in essentially equivalent amounts. Moreover, when sialic acid was removed from the 46 Kdalton app. MW HMFG antigen, its binding to virally infected cells was substantially reduced. This reduction in binding of the 46 Kdalton app. MW HMFG antigen to virus infected cells was found to be in the range of 30 to 60%. Thus, sialic acid may be required for the 46 Kdalton app. MW HMFG antigen to retain its binding activity as well as its anti-viral activity. Moreover, it is also possible that the anti-viral activity of milk mucins from other sources lacking sialic acid may be enhanced by sialylation. The polypeptide of this invention was also shown to inhibit in vitro viral infection of cells as well as viral gastroenteritis induced by viruses, e.g., rotaviruses, in an animal model. For instance, the administration of a murine rotavirus (EDIM) to suckling mice, caused a 100% incidence of diarrhea in the mice. However, the simultaneous administration of the virus and the human milk macromolecular or acidic glycoprotein fraction (containing the 46 Kdalton HMFG antigen) to the suckling mice, reduced the diarrhea symptoms by 90%. In contradistinction, when a bovine milk-based formula or a control medium were administered, the rotavirus activity and the diarrheal symptoms remained undiminished. The various components of the human milk fat globule may be purified as described in the art. The polypeptide of this invention may be easily prepared for clinical use either by purification, by recombinant techology or peptide synthesis. The polypeptide may be purified from biological sources as follows. Human breast milk may be readily fractionated by published methods into a macromolecular component comprising the fat gobule membrane. This component is distinct from oligosaccharides, lipids, immunoglobulins and other small proteins contained in milk. Likewise, whole human milk, the macromolecular fraction, and the fat globules may be defatted to produce fat globule membranes. The macromolecular fraction containing the milk mucin complex may be obtained by lipid extraction of fatty milk as described by Newburg, D. S., et al. (Newburg, D. S., et al, Pediatric Res. 31:22–28(1992)). The acidic glycoprotein fraction of milk may be obtained by isoelectric focusing as described by Yolken, R. M., et al. (Yolken, R. M., et al, J. Clin. Investigation 90: (1992)). Both these fractions have anti-viral activities that are, respectively, 3 and 38 times greater than whole milk. The milk mucin complex may be affinity-purified in accordance with published procedures (Ceriani et al., P.N.A.S.(USA) 74: 582–589 (1977)). Natural skim milk may be prepared by centrifuging unfrozen fresh milk, and removing the cream fraction that contains intact milk fat globules. When fresh milk is frozen and thawed, especially several times, sonicated, allowed to stand for a period of time, or exposed to temperature, the fat globules are generally disrupted. When the fat layer is then separated from the remainder or "processed skim milk", it contains mainly the lipid fraction of the cream (butter consisting of mainly triglycerides), while the milk fat globule membranes, the 70 Kdalton app. MW and the 46 Kdalton app. MW HMFG antigens are now mainly in the "processed skim milk". However, the amount is greatly increased in the "processed skim milk", the amount increasing with more vigorously freezing and thawing and/or sonication. Both the natural and the processed skim milk have anti-viral activity, with the latter evidencing higher activity. Curds and whey may be prepared as is known in the art, and will contain a certain proportion of the described components that have anti-viral activity. The milk mucin complex, in turn, may be further purified from the membranes using monoclonal antibodies as described herein, and the 46 Kdalton app. MW HMFG antigen may be separated from the milk mucin complex or prepared by recombinant technology as described herein or simply by expression in a host, either eukaryotic or prokaryotic, transfected with a hybrid vector carrying the polynucleotide segment of this invention or a fragment thereof. The natural components are separable by traditional chromatographic and/or electrophoretic methods. The presence and identities of the components of the human milk mucin complex are readily determined using available, specific monoclonal antibodies. The gene encoding the 46 Kdalton app. MW HMFG antigen being provided herein, the gene product and variations thereof may be prepared by recombinant technology and expressed in recombinant microorganisms, plant and mammalian hosts as described by Larocca et al. (Larocca et al., Cancer Res. 51:4994 (1991); Larocca et al. Hybridoma 11:191 (1992); Larroca, et al., "Molecular Cloning and eExpression of Breast Mucin Associated Antigens"", in Breast Epithelial Antigens, p. 36, Plenum Press, Ceriani, R. L., ed, New York, N.Y. (1991); and others). The amino acid sequence of the 46 Kdalton app. MW HMFG antigen is unrelated to any known immunoglobulin but was found to have significant homology to human epithelial cell proteins, the C1C2 domains of the human clotting factors V and VIII, the cell adhesion sequence RGD and an EGF-like sequence, a mouse milk fat globule 67 Kdalton app. MW protein MFG-E8, discoidin of amoebae, and the A5 antigen of xenopus brain, among others. Polypeptides having the viral binding characteristics of the 46 Kdalton app. MW HMFG antigen or fragments thereof may be prepared synthetically, by expression of genetically engineered vectors in trasfected hosts and/or by adding a stop codon at a desired place in the DNA encoding the protein, by methods known in the art, or by purification from human milk of the 46 Kdalton app. MW HMFG antigen and subsequent partial hydrolysis. The synthetic polypeptide having the described characteristics may be prepared in different lengths by alteration of the DNA sequence encoding it and adding a stop codon where desired, as is known in the art, and expression of the thus altered gene or fragments thereof. The cDNA encoding the 46 Kdalton app. MW HMFG antigen has been cloned and fully sequenced as disclosed herein.

The novel anti-viral agent of this invention is suitable for use in most instances of viral infections, and particularly in cases where other therapies are either ineffective or clinically contraindicated. The agent of this invention exhibits additional advantages for the treatment of infants and children since, as already indicated, its components are normal constituents of human milk and the human diet. The present agent is thus unlikely to elicit toxic, immunological or allergic reactions in treated subjects. Because these agents are innocuous to the human body, the invention may be used without intervention of skilled medical personnel, for example, by adding it to foodstuffs, and the like, that are normally sold over-the-counter in convenience stores or as food supplements available in grocery stores. This is a particular advantage for treating travellers or populations in underdeveloped countries where medical services are in short supply. The agent of this invention may be administered in combination with other treatments, such as immune therapy, particularly treatments that act by independent mechanisms, to thereby provide a multi-pronged attack on the virus. Other anti-viral treatments may be combined with the present agent to provide a treatment compatible with other clinical needs of a patient, as well. For example, other milk components, such as oligosaccharides, $\alpha$-interferon and trypsin inhibitors, known to have anti-microbial and anti-viral activity, may be combined with the present agent. The inventors have found that components of human milk other than those encompassed by the invention failed to inhibit rotavirus infection in cell cultures. These agents, prepared by methods described in the art, include lipids, gangliosides, polar neutral glycolipids, non-polar glycolipids, triglycerides and fatty acids and neutral, acidic and total oligosaccharides. The agent of the invention may be used alone, with a carrier or as an additive to a foodstuff, or in other compositions suitable for human consumption. Thus, an anti-diarrheic product may comprise a foodstuff, and an anti-viral effective amount of the polypeptide of the invention, either alone or in combination with other anti-viral agents and/or an agent selected from the group consisting of defatted human milk fat globules, skim milk, the human milk macromolecular fraction, curd, whey, the human milk mucin-70 Kdalton app. MW glycoprotein-46 Kdalton app. MW HMFG antigen complex, and mixtures thereof. Each additional agent may be used alone or combined with one or more of the agents provided herein, or further combined with a foodstuff or food supplement for self-administration. This composition may also be provided with other components including, but not restricted to, vitamin supplements, mineral additives, other nutritional additives, buffers, salts, flavoring compounds, diluents, thickeners, emulsifiers, preservatives, and anti-oxidants, such as would be familiar to a person skilled in the art, as would the amounts they are added in to the composition. The anti-diarrheic compostion or product may also comprise a binder such as gum tragacanth, acacia, corn starch or gelatin, excipients such as dicalcium phosphate, anti-clumping agents such as corn starch, potato starch, alginic acid and the like, lubricants such as magnesium stearate, sweetening agents such as sucrose, lactose or saccharin, flavoring agents such as peppermint, orange, wintergreen or cherry flavoring as well as other known artificial and natural flavoring compounds. Sustained-release preparations and formulations are also within the confines of this invention, and may contain further ingredients as is know in the art. A coated composition, or otherwise modified forms of the preparation are also contemplated herein such as coatings of shellac, gelatin, sugar and the like. Any material added to this product should be pharmaceutically-acceptable and substantially non-toxic in the amounts employed. Other excipients may be added to the formulation such as those utilized for the production of ingestible tablets, troches, capsules, elixirs, suspensions, syrups and wafers, among others and the product may then be provided in these forms. In one preferred embodiment, the polypeptide, whether glycosylated or non-glycosylated, may be compounded with other anti-viral human milk components as well as other anti-viral and anti-microbial agents as indicated above. In another preferred embodiment, the product comprises the mucin complex or mixtures thereof. The polypeptide of this invention may be present in the anti-diarrheic product in an amount of about 0.01 to 99.9 wt % of the composition, and preferably about 0.1 to 20.0 wt %. However, other amounts of the agent may also be present in the product. The amount of the agent in the anti-diarrheic product may be varied, and/or the frequency of administration increased, depending on the severity of the infection, the general health and nutritional status of the subject, and whether or not other anti-viral agents are being administered as well. Foodstuffs suitable for use in the anti-diarrheic product of the invention are milk, juices, cereals, chewing gum, crackers, candies, meats, vegetables and fruits, blended or otherwise as baby food for example, and cookies, among others. In another embodiment, the foodstuff of the product provided herein may be infant formula, milk, milk substitutes, baby foods, rehydration formula, and vitamin supplements, among others. This product may be specifically formulated for the palate of youngsters, when applied to the treatment of infants or small children.

The polypeptide may be provided in an anti-diarrheic kit comprising an anti-diarrheic composition comprising the polypeptide itself or a fragment thereof having anti-viral properties, either alone or with an agent selected from the group consisting of defatted human milk fat globules, skim milk, the human milk macromolecular fraction, curd, whey, the human milk mucin-70 Kdalton app. MW glycoprotein-46 Kdalton app. MW HMFG antigen complex, other anti-diarrheic agents and additives mentioned above, and mixtures thereof, and a pharmaceutically acceptable carrier; and instructions for its use. The anti-diarrheic composition of this kit may be administered in an amount of the anti-diarrheic product of about 0.1 to 1000 mg/kg body weight/day, and more preferably about 1 to 50 mg/kg body weight/day. Other amounts, however, may also be administered. It is understood that the more active fractions, such as the 46 Daltons app. MW HMFG antigen may be administered at a lower dose, whereas the lesser active fractions such as the defatted milk fat globule may be administered at a higher dose. Other amounts may also be administered. This kit is formulated for the therapeutic treatment of subjects afflicted with or at risk of diarrheal conditions associated with viral infection. The additives for the anti-diarrheic composition may be vitamin supplements, mineral additives, other nutritional additives, salts, buffers, flavoring compounds, diluents, thickeners, emulsifiers, preservatives, and antioxidants, among others, such as would be familiar to a person skilled in the art. Included within the invention, is an embodiment wherein the above anti-diarrheic compositions further comprise varying amounts of other components such as foodstuffs. Suitable are all kinds of foods including milk and milk supplements. The anti-diarrheic composition or the product of the invention may also be modified to include varying amounts of water and ingredients suitable to the clinical needs of the subject. The anti-diarrheic composition may be mixed with a drink, soup, and the like (liquid) or a foodstuff (solid) for self-administration. The composition may be added in an anti-viral amount, and may be provided in bulk or in unit form. An anti-diarrheic kit is also provided that comprises in separate, containers, a foodstuff, and an anti-viral effective amount of the polypeptide of the invention, either alone or with an agent selected from the group consisting of defatted human milk fat globules, skim milk, the human milk macromolecular fraction, curd, whey, the human milk mucin-70 app. MW glycoprotein-46 Kdalton app. MW HMFG antigen complex, and mixtures thereof, and optionally a pharmaceutically-acceptable carrier, and instructions for use of the kit. For purposes of identification of the components, the apparent molecular weight (app. MW) of the glycoproteins of the invention may be determined by SDS-polyacrylamide gel electrophoresis using standard techniques described in the art. For example, defatted human milk fat globule membranes may be dissolved in a solution containing 1% sodium dodecyl chloride (SDC) and heated to disolve the glycoproteins, applied to a 3–30% polyacrylamide gel and electrophoresed with appropriate molecular weight standards run in a parallel lane, the apparent molecular weight (app. MW) of the mucin complex obtained is approximately 400,000 Kdalton app. MW or greater. The apparent molecular weights of other proteins may be determined in a similar manner. The 46 Kdalton and the 70 Kdalton app. MW glycoproteins associated with the milk mucin complex may also be identified by binding to the specific monoclonal antibodies Mc16 and Mc13, respectively (Larocca et al., Cancer Res. 51:4994 (1991); Peterson et al., Hybridoma 9:221–235 (1990), supra). The milk mucin, also referred to as breast mucin, may be identified in the complex by binding to the monoclonal antibody Mc5 described by Peterson, J. A., et al. (Peterson, J. A., et al., Hybridoma (1990), supra). If the defatted human milk fat globule is disolved in SDS under reducing conditions such as in the presence of 0.5% beta-mercaptoethanol, the 70 Kdalton app. MW HMFG glycoprotein runs as a doublet with an apparent molecular weight of 70 Kd, that may be further identified by binding to the monoclonal antibodies Mc13 and McR2. The 46 Kdalton app. MW HMFG glycoprotein under the same conditions, appears as a doublet with an apparent molecular weight of 46 Kd, as identified by binding, among other antibodies evidencing specificity for different epitopes on the molecule, to the monoclonal antibodies Mc3 and Mc16 described by Larocca, et al. (Larocca et al., Cancer Res. 51:4994 (1991), supra). The milk mucin, under reducing conditions, is seen as a band of approximate 400,000 Kdalton apparent molecular weight and may be identified by binding to the monoclonal antibody Mc5 described by Peterson, J. A., et al. (Peterson, J., et al., Hybridoma (1990), supra). If the milk mucin, the 70 Kdalton app. MW HMFG glycoprotein, and the 46 Kdalton app. MW HMFG glycoprotein are treated to remove oligosaccharides, their apparent molecular weights, as determined by polyacrylamide gel electrophoresis, appear to decrease. This invention additionally provides a method for retarding the onset of, or countering, viral infection, such as that associated with rotaviruses, of a mammalian cell comprising contacting the cell in a nutrient medium with an anti-viral infection effective amount of the polypeptide of this invention or fragments thereof, either alone or with an agent selected from the group consisting of defatted human milk fat globules, skim milk, the human milk marcomolecullar fraction, curd, whey, the human milk mucin-70 Kdalton app. MW glycoprotein-46 Kdalton app. MW HMFG glycoprotein complex, and mixtures thereof. In one preferred embodiment of the invention, the anti-diarrheic composition comprises the 46 Kdalton app. MW HMFG glycoprotein. In another embodiment, the composition comprises the polypeptide of this invention and the mucin complex. Both of these agents may be administered alone and/or with defatted human milk fat globules, and/or whey, and/or curd, and/or skim milk, and/or the HMFG macromolecular component, and/or the 46 Kdalton app. MW HMFG glycoprotein, fragments thereof having anti-viral activity, and/or mixtures thereof. Although the complete removal of glycosides from the mucin complex was shown to reduce the anti-viral activity of the glycoprotein by at least 40–60%, agents having varying levels of glycosylation may be used, since they retain some activity. Also disclosed herein is a method of retarding the onset of, or countering, viral infection of a subject's cells comprising administering to a subject at risk for, or suffering from, a viral infection, such as a rotavirus infection an anti-viral effective amount of the composition of this invention or mixtures thereof, or a composition comprising the polypeptide of the invention and a pharmaceutically-acceptable carrier and/or a foodstuff and/or other additives as described above. The composition may incorporate other anti-viral or anti-microbial agents, as suitable for effective treatment of a rotavirus infection taking into account the age, general health, and nutritional status of the subject. Other compositions of the agent of the invention and further comprising, e.g., the macromolecular fraction of the defatted milk fat globule membrane and the acidic fraction, are also contemplated herein.

The onset of, or countering, infantile gasteroenteritis associated with viral infection, such as rotaviral infection, may be retarded or completely prevented by administration to an infant or child in need of the treatment an anti-viral infection effective amount of the polypeptide of the invention, either alone or with an agent selected from the group consisting of defatted human milk fat globules, skim milk, the human milk macromolecular fraction, curd, whey, the human milk mucin-70 Kdalton app. MW glycoprotein-46 Kdalton app. MW HMFG antigen complex, and mixtures thereof, and optionally a pharmaceutically-acceptable carrier and/or other agents and infant foodstuffs such as formula, milk, juice, and the like, as described above. The above method may be used for the prophylaxis of the disease, particularly where demographic and public health information suggests significant risk of infection. When symptoms indicate the onset of infection, the method may also be applied therapeutically. The agent of this invention may be present in the infant formula in an amount from 0.01 to 99.9 wt %, and more preferably about 0.1 to 2.0 wt % of the composition. Other amounts of the agent, however, may also be used. As this product is formulated for the prophylatic or therapeutic treatment of infants and children afflicted with or at risk of diarrheal conditions associated with viral infection, the infant food product may include varying amounts of infant formula, juices, foods, milk or milk supplements, among others. This anti-diarrheic infant product may also include vitamin supplements, water, mineral and other nutritional additives, salts, buffers, flavoring compounds, diluents, thickeners, emulsifiers, preservatives, encapsulation agents, glycosidase inhibitors, protease inhibitors, and anti-oxidants, such as would be familiar to a person skilled in the art. The infant formula may also be modified to include varying amounts of water and other solutes to meet other clinical needs of the infant or child. The human milk components of this invention being routinely consumed and consisting of biological molecules, their administration will neither require clinical precautions nor medically trained personnel. Accordingly, the present products may be sold over the counter. Also provided herein is a method of retarding the onset of, or countering, diarrhea associated with viral infections, such as rotavirus infection, in a subject's cells comprising administering to a subject in need of such treatment a composition comprising an anti-viral effective amount of the polypeptide of the invention, either alone or with an agent selected from the group consisting of defatted human milk fat globules, skim milk, the human milk macromolecular fraction, curd, whey, the human milk mucin-70 Kdalton app. MW antigen-46 Kdalton app. MW HMFG antigen complex, and mixtures thereof, and optionally a pharmaceutically-acceptable carrier and/or a foodstuff. Because of minimal side effects associated with the agent used in this method, the agent may also be administered for diarrheal symptoms regardless of etiology to prevent secondary outbreaks associated with rotavirus infection. The polypeptide of the invention is also suitably applied to retard the onset of, or counter, diarrhea associated with viral infection in an immunodeficient subject comprising administering to an immunodeficient subject an anti-viral effective amount of the polypeptide, either alone or with an agent selected from the group consisting of defatted human milk fat globules, the human milk macromolecular fraction, skim milk, curd, whey, the human milk mucin-70 Kdalton app. MW antigen-46 Kdalton app. MW HMFG antigen complex, and mixtures thereof, optionally comprising a pharmaceutically acceptable carrier and/or foodstuffs as described above. Such immunodeficiencies may result from genetic dysfunction, organ transplant, disease induced conditions or as a consequence of medical treatment with drugs, among others. Other agents that may be added to the composition for this particular application are bulking agents, carbon black, high fiber additives, encapsulation agents, protease inhibitors, glycosidase inhibitors, and carrier lipids, optionally micellar, among others. These may be present in amounts known in the art. Specific applications of the above method are in cases of, e.g., transplants such as bone marrow, kidney, heart and other organ transplants. Transplant patients receiving immunosuppressant drugs may also benefit from this anti-diarrheic treatment. The above preventative and therapeutic methods may be practiced by administering the agent provided herein as part of an anti-diarrheic composition also comprising a carrier or a product such as a foodstuff, as described above. Suitable foodstuffs are milk, juices, cereals, powdered grains, candies, confections, cookies, meats, vegetables and fruits, put through a blender or otherwise processed, and crackers, among others.

A pharmaceutical or foodstuff composition for preventative, therapeutic, and/or imaging purposes may comprise the polypeptide of the invention and a non-proteolytic carrier. The carrier may be a pharmaceutically-acceptable carrier or in some cases a foodstuff. This composition may be produced in bulk or in unit form. In the latter case, each unit may contain an antibody binding effective amount (in vitro and ex vivo assays), an anti-viral effective amount (anti-viral therapy), or an anti-cancer therapeutic amount (cancer therapy) of the polypeptide. The pharmaceutical or foodstuff composition is intended for in vivo animal use, which includes human administration. Each dose preferably contains about 0.1 to 1000 mg of the polypeptide per kg body weight, and more preferably about 10 to 500 mg/kg. However, other amounts may also be administered as a practitioner would know. Any pharmaceutically-acceptable carrier may be utilized for the preparation of the composition intended for in vivo therapy or diagnostic use. Examples of suitable carriers and other additives are flavorings, preservatives, bulking materials, stabilizers, adjuvants, coatings, colorants, and salt solutions such as saline, oils or solids, among others as known in the art. However, any liquid or solid carrier which does not hydrolyze the polypeptide is suitable particularly for in vitro and ex vivo uses. The pharmaceutical or foodstuff composition as well as the polypeptide itself are best kept under refrigeration and/or frozen as is known in the art. The polypeptide and the pharmaceutical or foodstuff composition may be vacuum dried and packaged in a sterile container for transportation to their destination. The composition may comprise about 0.01–99.99 wt % of the polypeptide, and preferably about 0.1–10 wt %, the remainder being the carrier when the composition is intended for in vitro application only, in which case the carrier need only be non-proteolytic. Also provided herein is a fusion protein, which comprises the polypeptide described above, and a second antigenic polypeptide or an antibody binding fragment thereof which is operatively bound to the polypeptide. The polypeptide of the invention may be bound to a fragment of the second antigenic polypeptide as peptides about 10 to 1000 amino acids long and 10 to 1100 amino acids long, respectively, and preferably about 15 to 300 amino acids long and 200 to 400 amino acids long, respectively. However, other sizes of the polypeptides, and/or fragments thereof, either larger or smaller, may be utilized as long as their antibody binding capability is preserved. Any polypeptide is suitable as the second antigenic polypeptide as long as it acts as an antigen to elicit the formation of antibodies by a mammal when intended for use in a multiple antibody assay. The second antigenic polypeptide may also be chosen by some other property suitable for the identification and/or use of the fusion protein, such as a function other than antigenicity. By means of example, the second antigenic polypeptide may be a protein such as β-galactosidase or a fragment thereof. Both, the polypeptide of the invention and the fusion protein may be prepared by methods known in the art, either synthetically or by expression of a DNA fragment that encodes it as described herein or by cloning and expression utilizing other methods known in the art. The fusion protein may be prepared, for instance, by cloning a recombinant DNA encoding, in reading frame, the gene's segment into a vector carrying the DNA encoding the second polypeptide, transfecting a suitable host, and expressing it in a host.

Also part of this invention is an antibody having high affinity, selectivity and specificity for the 46 Kdalton HMFG antigen of the invention or fragments thereof containing one or more of its epitopes. These antibodies are of greater specificity for cancer cells than the original antibodies used to isolate the mRNA because they identified epitopes on the polypeptide that are probably more accessible to the antibody when the polypeptide is on the cell. Monoclonal antibodies Mc8 and Mc 16 bind to the C1C2 domain of the 46 Kdalton HMFG antigen, that is considered to be the domain most likely buried in the cell membrane. Also antibodies against the cell adhesion sequence RGD and the EGF-like sequence are intended for modifying the function of the 46 Kdalton HMFG antigen in cancer cells and thus diminish the cancerous properties of these cells. Also, the antibodies that bind to more accessible epitopes evidence greater applicability in immunohistochemistry. Methods for raising antibodies are known in the art and need not be described herein. For instance, the amino acid sequence corresponding to a desired epitope may be utilized as a hapten or antigen and with the aid of a carrier protein and adjuvants administered to an animal to raise epitope-specific antibodies. The B-cells producing these antibodies may then be utilized to produce hybridomas by methods known in the art that express highly specific antibodies for selected epitope. Particularly preferred are monoclonal antibodies. The antibodies raised against the biologically pure polypeptide or epitopic fragments thereof have increased affinity and/or specificity for the polypeptide. Typically, the affinity constant may be about $10^8$ to $10^5 M^{-1}$, and in some cases greater than $10^8 M^{-1}$. Particularly preferred embodiments of the antibody also have affinity for the C1 and/or C2 regions of clotting factor VIII (light chain) and the RGD and/or EGF-like segments thereof. Still another preferred antibody of the invention are binding active Fab, (Fab)$_2$, and Fab' fragments thereof. Also preferred are binding active single chains of the antibody or the fragments. A composition intended for in vitro use comprises an anti-46 Kdalton HMFG antigen antibody having an affinity constant of about $10^{10}$ to $10^5 M^{-1}$, or binding fragments thereof, and a non-proteolytic carrier. When intended for in vivo or ex vivo use, the carrier must be a pharmaceutically-acceptable carrier or a foodstuff. When in unit dose form, the antibody is typically provided in an amount of about 0.001 to 100,000 mg, and more preferably about 10 to 500 mg. However, other amounts are suitable. Any pharmaceutically-acceptable carrier is suitable as indicated above. Other ingredients may also be contained in the composition such as radionuclides, chemotherapeutic drugs, interferon, toxic agents such as ricin A-chain, abrin A-chain, saline salt solutions, preservatives, flavors, bulking agents, colorants and buffers, among others, as is known in the art. The preparation of all the compositions may be undertaken by admixing the polypeptide or the antibody with the pharmaceutically-acceptable carrier under non-proteolytic conditions, then vacuum dried and packaged in sterile containers or provided as a sterile solution.

The present antibodies may be applied to detecting the presence in a biological sample of the 46 Kdalton HMFG antigen or fragments thereof, by addition to a biological sample suspected of containing the polypeptide, adding thereto an antibody selectively binding the 46 Kdalton HMFG antigen under conditions effective to form an antibody-polypeptide complex, determining the amount of complex formed, and preparing the result with a control run without the sample. This method is suitable for detecting the presence of the polypeptide or fragments thereof in biological samples such as animal cells, cell extracts, body fluids such as milk, and aids in the determination of whether epithelial cells or neoplastic tumor cells such as those from breast and other tissues which are of epithelial origin and express the 46 Kdalton HMFG antigen, are present in the sample. Typically, all body fluids are encompassed herein. Examples are serum, plasma, urine, breast fluid, human milk, tissue biopsies, and fine needle aspirates. The sample may be previously treated, e.g., to avoid interference by metals, non-specific proteins, fats, nucleic acids, and the like as is known in the art. The biological sample may also be diluted in order that the protein content be in a range of about 0.0001 to 10 mg/ml, and more preferably about 0.001 to 0.1 mg/ml. The antibody may be added in an amount of about 0.0001 to 1.0 mg/ml of sample, and more preferably about 0.001 to 0.1 mg/ml of sample. Other conditions for the assay utilized, including the following. The sample may be homogenized and centrifuged to remove particulate material and fatty material. Detergents may be added to dissolve membranes, solubilize fatty material and reduce background. Also added may be carrier proteins such as bovine serum albumin to reduce non-specific binding of the antibodies, and chelators to remove interfering divalent metal ions. The antibody may be monoclonal or polyclonal, although preferred are monoclonal antibodies which provide high sensitivity. Even more preferred are antibodies of affinity constants of about $10^8$ and up to about $10^{10} M^{-1}$. The determination of the presence of any complex formed between the antibody and the polypeptide may be done by a variety of methods known in the art. By means of example will be cited herein the further addition of a labeled anti-constant region immunoglobulin to form a labeled double antibody-polypeptide complex. The label may be a radiolabel, a fluorescent label, an enzyme label or biotin to be later detected as a conjugate of avidin, streptavidin or magnetic bead, among others. After this step, the amount of label bound to the complex may be assessed by methods known in the art. This method may be applied to determining the presence in a biological sample of epithelial cells or the 46 Kdalton HMFG atnigen itself or a fragment thereof by adding to a biological sample suspected of containing cells of epithelial origin or the antigen or a fragment thereof such as cancer patient's serum samples an anti-46 Kdalton HMFG antigen antibody, and determining the amount of any complex formed therebetween. This method is particularly well suited for biological samples such as bone marrow, milk and serum samples. However, it may be practiced with samples of other origins as well. The steps are in general conducted as described above and the determination of the presence of malignant tumor cells of epithelial origin or anti-viral factors in milk may be done by the identification, either qualitative or quantitative, of any complex formed with the antibody as already described. The detection may also be undertaken by assaying for the presence of ribonucleic acid (RNA) encoding the 46 Kdalton HMFG antigen using nucleic acid probes based on sequences such as the ones shown in Table 1 and 4 or fragments thereof, and methods known in the art such as PCR (Erlich, H. A., in PCR Technology: Principles and Applications for DNA Amdification, Stockton Press (1989)).

The antibody may also be applied to the in vivo imaging or therapy of malignant tumors of epithelial origin by administering to a subject suspected of being afflicted by a cancer of epithelial origin, or undergoing cancer therapy, a polypeptide binding effective amount of an anti-46 Kdalton HMFG antigen antibody of this invention effective to deliver it to an area of the subject's body suspected of having the neoplastic tumor to form an antibody-cell polypeptide complex. The antibody may carry a radiolabel or other anti-cancer therapeutic agent or a detectable label capable of binding to the antibody at a site other than polypeptide binding site may be administered, and then non-invasively detecting the presence of the label associated with any complex formed in the subject's body. The antibody may be administered at a concentration of about 0.5 to 50 mg/ml, and more preferably about 5 to 20 mg/ml. A total of about 1 to 50 ml of the antibody composition may be given at any one particular time. The regimen of administration may be by single or repeated dosage, or the antibody may be administered in a continuous manner in order to image or to continuously suppress the presence of tumor cells. The antibody may be administered in a pharmaceutical composition as described above, or in any other suitable form. The administration of the antibody may be conducted by intravenous, intraperitoneal, intracavitary, lymphatic, intra-tumor or intramuscular routes, among others. Other routes are also suitable if they do not hydrolyze the peptide links of the antibody. The administration of a detectable label may be conducted by utilizing a labeled anti-constant region immunoglobulin, protein G or A or a binding fragment thereof, and then detecting the amount of label bound to the complex. These technologies are known in the art and need not be further described herein.

The polypeptide and fusion protein of the invention may be applied to detecting the presence in a biological sample of anti-46 Kdalton HMFG antigen antibodies, indicative of a growing neoplastic tumor of epithelial origin such as a carcinoma, by adding to a sample obtained from a patient suspected to be afflicted with this type of cancer an antibody binding effective amount of the polypeptide of the invention and determining the presence of any complex formed. The sample may be treated as indicated above to eliminate interference by other proteins and/or components present in the sample. In the case of blood, serum may be obtained first, and then the serum may be treated by adding normal human or bovine serum, and/or bovine serum albumin (BSA) is used as a blocking agent to reduce non-specific reactivity. The polypeptide may be recombinantly produced and is typically added to the sample in an amount of about 0.00001 to 1.0 mg/ml sample, and more preferably about 0.0001 to 0.1 mg/ml sample. However, other amounts may also be utilized as seen for different assay procedures, and the amount of antibody in the sample may be controlled by dilution. Optimal ranges of antibody in the sample are about 0.00001 to 0.1 mg/ml, and more preferably about 0.0001 to 0.01 mg/ml, but, other amounts may also be utilized. The steps of this method are practiced as described above, including the determination of the presence of antibody-polypeptide complex. The conditions for the assay are in general those known in the art for not denaturing proteins and the overall variables, such as pH, temperature and the like may be adjusted without undue experimentation. The presence of an anti-46 Kdalton HMFG antigen antibody in a sample may also be detected by adding to a sample suspected of comprising the antibody a binding effective amount of the fusion protein of this invention under conditions effective to form an antibody-fusion protein complex, adding thereto an anti-second polypeptide antibody under conditions effective to form a double antibody complex, and determining the presence of any double antibody complex formed. This method is preferably practiced with an anti-second polypeptide monoclonal antibody. The amount of anti-second polypeptide antibody added to the sample is preferably about 0.00001 to 0.1 mg/ml sample, and more preferably about 0.0001 to 0.01 mg/ml of sample. However, other amounts may also be utilized, and the sample may be pretreated prior to the addition of the fusion protein in various manners, such as by dilution and/or elimination of interfering components. These steps are undertaken as is known in the art and need not be further described herein. Solid-phase type of assays are preferred, and among these, more preferred is the Ceriani et al. method (Ceriani, R. L. et al., Anal. Biochem. 201:78 (1992)). However, other assays are also suitable and therefor, contemplated herein.

The polypeptide of the invention is also useful for vaccinating against neoplastic tumors and cancer by its administration or that of antigenic fragments thereof in amounts effective to elicit an endogenous immunological response. This in vivo method may also be utilized in cancer patients to induce an immune response against their exposed neoplastic epithelial cells carrying the corresponding epitopes. The vaccinating polypeptide may be administered to a subject including a human in an amount of about 0.1 to 100 mg/ml, and more preferably about 2 to 50 mg/ml. Typically, any dose may be delivered in about 0.1 to 50 ml, and more preferably in about 1 to 10 ml of the carrier. The vaccinating composition may be administrated in a single dose or it may be administered repeatedly and/or on a continuous basis for periods of up to about 6 months, and sometimes in excess of one year, alone with a carrier or in conjunction with one or more adjuvants, and the like, as is known in the art. More prolonged periods of time are also encompassed for vaccination according to this invention.

A therapeutic agent may be delivered in vivo to target epithelial cells, such as neoplastic cells by binding it to the anti-46 Kdalton HMFG antigen monoclonal antibody provided herein at a site other than the antigen binding site, administering to a subject afflicted with a neoplastic growth of epithelial origin a therapeutically effective amount of the antibody-bound therapeutic agent under conditions effective to deliver the agent to the target cells environment, and allowing the antibody carrying the therapeutic agent to bind to the target cells to permit the therapeutic agent to exert its effect on the cells. This in vivo method may be utilized for treating cancer patients that are afflicted with cancers of epithelial origin, e.g. breast cancer. The therapeutic agent may be any anti-cancer agent known in the art, such as radionuclides, chemotherapy drugs, toxic agents such as ricin A-chain, abrin A-chain, and others. The therapeutic agent is typically bound to the antibody by means known in the art. More specifically, a radionucleide such as $^{131}I$ may be bound to the antibody by oxidation of amino acids such as tyrosine, or $^{90}Y$ may be attached via a chelator, and the conjugate injected intravenously or intraperitoneally into humans afflicted with neoplastic tumors such as breast carcinomas among others to inhibit the growth of the tumor. (e.g., for mice, Ceriani, et al, Cancer Res. 48:4664–4672 (1988)). The antibody-bound therapeutic agent may be administered to the subject in an amount of about 1 to 100 mg/ml, and more preferably about 2 to 20 mg/ml. Typically, any dose will consist of about 1 to 50 ml of carrier and more preferably about 2 to 10 ml carrier. The antibody-bound therapeutic agent may be administered as a single dose, in multiple doses, or on a continuous basis for periods of up to about 6 months, and sometimes in excess of one year. More prolonged periods of time are also encompassed for treatment herein.

The therapeutic agent may also be delivered ex vivo to target cells such as neoplastic tumor cells by adding the antibody-bound therapeutic agent to a sample obtained from a patient afflicted with cancer under conditions effective to promote the formation of an antibody-cell polypeptide complex, allowing the agent to exert its effect on the cells, and returning the sample to the subject. Non-conjugated antibody may also be added to the sample in the presence of complement, which causes lysis of the cells, prior to returning the sample to the subject. In general, the steps of this method may be practiced as described above for other applications, particularly in terms of the preparation of the biological sample, and binding of the therapeutic agent to the antibody as well as the addition of the antibody-bound therapeutic agent to the sample. The sample may be returned to the subject by means known in the art. For example, the already treated sample may be returned to a subject's body in sterile form by the intravenously, intracavitary, intraperitoneal, and intratumor routes, among others. However, other routes known in the art may also be utilized.

Also provided herein is a polynucleotide encoding the polypeptide of this invention including all redundant DNA and RNA sequences. The polynucleotide is provided either as a double stranded or single stranded DNA containing the coding or the non-coding strand of the polynucleotide. The fragments of the polynucleotide may be of about 15 to 3000 bases, and more preferably about 30 to 300 bases. Both the double stranded and the single stranded DNAs discussed above may be in labeled form. The labeling may be conducted as is known in the art with radioactive atoms such as $^{32}P$, $^{14}C$, $^{3}H$, $^{33}P$, and the like. However, other radionuclides may also be utilized. Particularly preferred is a polynucleotide encompassing the DNA sequence shown in Tables 1 and 4 of this patent and redundant sequences thereof encoding the polypeptide of the invention or fragments thereof comprising about 9 to 3000 bases, and more preferably about 18 to 300 bases. However, fragments of other sizes may also be utilized and are encompassed herein. Also part of this invention is a polyribonucleotide encoding the polypeptide of the invention or fragments thereof. The polyribonucleotide segments may be about 9 to 3000 bases long, and more preferably about 18 to 300 bases long. However, other fragment sizes are also encompassed herein. Still part of this invention is a non-coding strand of a polyribonucleotide having a sequence complementary to that of the polyribonucleotide described above. This polyribonucleotide sequence is capable of hybridization to the coding RNA strand or to the non-coding strand of the corresponding DNA. In a particularly preferred embodiment the polyribonucleotide is provided in labeled form.

A hybrid polynucleotide encoding a fusion protein comprising the above polypeptide and a second antigenic polypeptide or antibody binding functional fragment thereof bound thereto. The hybrid polynucleotide may be about 15 to 4000 bases long, and sometimes longer, and more preferably about 50 to 1,800 bases long. However, other size polynucleotides are also encompassed herein. Also provided herein is a hybrid polyribonucleotide encoding a fusion protein comprising the polypeptide of the invention and a second antigenic polypeptide, or antibody binding fragment thereof bound thereto and all redundant fragments thereof and complementary sequences thereof. The hybrid polyribonucleotide encoding the fusion protein may be about 15 to 4000 bases long, and more preferably about 50 to 1,800 bases long. Fragments thereof may be about 9 to 100 long, and more preferably about 15 to 70 bases long. The hybrid polynucleotide encoding the fusion protein is provided as a double stranded DNA which encompasses the coding or non-coding strand encoding the fusion protein or fragments thereof. The latter polynucleotide provided herein is a polynucleotide comprising DNA sequences complementary to the polynucleotide encoding the fusion protein. Both the DNA and RNA sequences encoding the fusion protein may be provided in labeled form. Particularly useful labels are $^{32}P$ and others known in the art. The DNAs and RNAs are labeled by methods known in the art.

The presence of a polynucleotide encoding the 46 Kdalton HMFG antigen or a fragment thereof in a sample may be detected by adding to the sample a hybridization effective amount of a labeled DNA comprising the non-coding strand of a polynucleotide encoding the polypeptide or hybrid polypeptide of the invention under stringent conditions effective to hybridize any polynucleotide having a complementary sequence of at least 15 bases thereto, and detecting the presence of the DNA-complementary polynucleotide hybrid. The sample may be a biological sample or it may be a laboratory sample. If the sample contains cells where the polynucleotide is located, the cells may need to be lysed, and optionally the DNA isolated from the remainder materials. This may be done by methods known in the art. The sample may be diluted and/or otherwise prepared for the melting of double stranded polynucleotide sequences present therein. The melting step is conducted as is known in the art. In general, the sample is prepared by lysing the cells in 4M guanidinium isothiocyanate to denature protein and prevent RNAse activity. Extracts are run on a cesium chloride density step gradient ultracentrifugation where RNA, DNA and protein are separated according to their relative densities. DNA and RNA may be further purified by extraction with organic solvents, and concentrated by precipitation in 70% ethanol. (Sambrook et al, in Molecular Cloning: A Laboratory Manual, Second edition, Cold Spring Harbor Press, N.Y., (1989)). Melting may be accomplished by raising the temperature of the sample about 20° C. over the Tm of the DNA, or by raising the pH to above 12. To the melted DNA may be added a hybridization effective amount of the labeled non-coding DNA strand. Suitable conditions for the hybridization of DNA-DNA segments are known in the art. The degree of stringency is determined by the degree of complementarity of the sequences desired to be hybridized. In general, when more stringent conditions are utilized hybridization will occur only with DNA sequences which have a high degree of complementarily with the probe. Thus, a low degree of stringency is desired to detect sequences with low complementarity, and the conditions may be varied accordingly. In general, the conditions may be as follows. The sodium ion concentration is about 1M, the pH about 5–9, the temperature about 65° C. or about 20° C. below the melting temperature of the duplex DNA of the probe sequence and its complementary strand (Britten, R. et al, Methods in Enzymology 29:363(1974); Sambrook et al, supra). The DNA-complementary polynucleotide labeled hybrid may be detected by methods known in the art. Typically, the double stranded DNA is restricted with enzymes and electrophoresed on a gel to separate the different size fragments. The gel is blotted onto a specially prepared filter, hybridized, and the filter is then exposed to a photographic plate for an effective period of time. The plate is then developed and the different fragments analyzed. For a more qualitative detection of the presence of the double stranded labeled hybrid, the unrestricted DNA may be blotted onto a filter, hybridized, exposed to a photographic plate and the plate developed to merely detect the presence of radiolabel.

The presence of an RNA sequence encoding the 46 Kdalton HMFG antigen or a fragment thereof may be determined by adding to a sample suspected of containing the RNA, a hybridization effective amount of the coding strand of a labeled polynucleotide encoding the 46 Kdalton HMFG hybrid polypeptide or fragment thereof antigen in single stranded form under stringent conditions effective to hybridize any RNA having a complementary sequence of about at least 15 bases thereto, and detecting the presence of the polynucleotide-RNA hybrid. In essence, this method is conducted as previously described for detection of a DNA sequence, with the additional precaution of substantially ensuring the absence or RNAses in the mixture. In general, the following must be additionally done when detecting RNA. The use of RNAase inhibitors and the pretreatment of labware with diethylpyrocarbonate to inactivate any contaminating RNAase. Hybridizations are conducted generally at a higher stringency because RNA:RNA hybrids are more stable than DNA:DNA hybrids. For example, the hybridization may be conducted at 65° C. in 50% formamide. The Tm of DNA duplexes is reduced by about 0.72° C. per 1% formamide added. (See, Sambrook et al, supra; Casey J. and Davidson N., Nucl. Acids Res. 4:1539–1552(1977)). If the RNA is contained inside the cells, the cells must be lysed to expose the ribonucleic acid. This is done by means known in the art such as detergent lysis, which may be followed by treatment with proteases.

Also part of this invention is a DNA segment comprising an anti-sense polynucleotide to the coding strand of the polynucleotide of the invention of about 200 to 1,800 nucleotides. More preferably, the DNA segment may have about 100 to 1,000 nucleotides. The concept of anti-sense sequences is generally known in the art. Synthetic oligonucleotides may be prepared that are complementary to the messenger RNA encoding a target protein. The oligonucleotide or a chemically modified equivalent thereof are then added to cells. The oligonucleotide binds the target mRNA and thus inhibits the translation of the target protein. (Markus-Sekura C. J., "Techniques for using Antisense Oligonucleotides to Study Gene Expression", Analytical Biochemistry 172:289–295(1988)). Alternatively, antisense-RNA may be used to block translation of sense RNA. The antisense RNA may be generated from a viral or plasmid DNA vector that contains a copy of the target gene situated in the reverse orientation with respect to the direction of transcription. A virus may be used as a carrier to introduce the inverted gene into the target cell gerome. (Izant, J. G. and Weintmub H., Science 229:345–352(1985)). Fragments of the anti-sense DNA segment are also provided herein and they may comprise about 15 to 100 bases, and more preferably 30 to 50 bases. The anti-sense sequences may be obtained by methods known in the art such as the following. Antisense oligonucleotides can be made by modifying their phosphate moiety to increase biological lifetime, to enhance the permeability of the cells and to strengthen binding to the target. For example, oligomethylphosphonates (Miller, P. S., Reddy, M. P., Murakami, A., Blake, K. R., Lin, S. B. and Agris, C. H. (1986) Biochemistry 25:5092–5097), or oligo-phosphorothionates (LaPlanche, L. A., James, T. L., Powell, C., Wilson, W. D., Uznanski, B., Stec., W. J., Summers, M. F. and Zon, G. (1986) Nucleic Acids Res. 14:9081–9093), or fragment thereof, a pharmaceutically-acceptable carrier. The composition may comprise different amounts of the components. Typically, the anti-sense DNA is contained in an amount of about 0.01 to 99.99 wt %, and more preferably about 0.1 to 20 wt % of the composition, the remainder being carrier and/or other known additives. The pharmaceutically-acceptable carrier may be any carrier which does not degrade DNA and is physiologically tolerated. Examples of carriers and other additives are sterile buffered saline solution, human serum albumin and the like. However, others may also be utilized. The pharmaceutical composition may be prepared by admixing the anti-sense DNA with the carrier and other components as is known in the art, freeze dried and packaged in a sterile container. The composition may be maintained refrigerated and/or frozen. The anti-sense product may be applied to the treatment of cancer of epithelial origin by administering it as a composition comprising a therapeutically effective amount of the anti-sense DNA segment of this invention or a fragment thereof. This method may be practiced by administering about 5 to 800 mg anti-sense DNA per day, and more preferably about 20 to 200 mg anti-sense DNA per day in a pharmaceutical composition. The composition may be administered by a parenteral, intravenous, intracavitary or other localized route. However, other routes of administration may also be utilized.

Part of this invention is also an immunoassay kit comprising, in separate containers, a monoclonal antibody having specificity for the 46 Kdalton HMFG antigen of this invention or Fab, (Fab)$_2$, or Fab' fragments thereof, anti-constant region immunoglobulin, protein G or A or binding fragments thereof for use with entire antibodies, and instructions for its use. This immunoassay kit may be utilized for practicing various of the methods provided herein. The monoclonal antibody and the anti-constant region immunoglobulin or other antibody binding molecules may be provided in amounts of about 0.001 mg to 100 grams, and more preferably about 0.01 mg to 1 gram. The anti-constant region immunoglobulin and other antibody binding molecules may be a polyclonal immunoglobulin, protein A or protein G or functional fragments thereof, which may be labeled prior to use by methods known in the art. The antibody may also be provided as an immunotherapy kit, comprising in addition, in separate containers, a therapeutic agent such as an anti-cancer agent and instructions for using the kit and for attaching either the therapeutic agent or a radiolabel to the antibody or to a further component such as immunoglobulin, protein G or A or binding fragments thereof.

Also provided herein is an antibody detecting kit comprising, in separate containers, a polypeptide having the antibody binding specificity of the 46 Kdalton HMFG antigen, anti-constant region immunoglobulin, protein G or A or fragments thereof, and instructions for its use. The polypeptide may be a recombinantly obtained peptide and the anti-antibody immunoglobuiin may be labeled prior to use. A fusion protein kit comprises, in separate containers, the fusion protein of this invention, an anti-second polypeptide monoclonal antibody, anti-constant region immunoglobulin, protein G or A or binding fragments thereof, and instructions for its use. The fusion protein may be provided in sterile form in an amount of about 0.001 mg to 100 grams, and more preferably about 0.01 mg to 1 gram. The anti-second polypeptide monoclonal antibody may also be provided in sterile form in an amount of about 0.001 mg to 100 grams, and more preferably about 0.01 mg to 1 gram. The anti-constant region immunoglobulin, protein G or A or fragments thereof may be provided in a separate sterile container in an amount of about 0.001 mg to 100 grams, and more preferably about 0.01 mg to 1 gram. The entire kit may be packaged for shipping and storage. An anti-cancer therapeutic kit provided according to this invention comprises, in separate containers, a monoclonal antibody selectively binding the 46 Kdalton HMFG antigen, an anti-cancer agent selected from the group consisting of immunotoxins and radionuclides and instructions for its use. The monoclonal antibody may be provided in sterile form in an amount of about 1 mg to 20 grams, and more preferably about 2 mg to 10 grams. The antibody may be freeze-dried and packaged and the therapeutic agent may be any known anti-cancer agent. By means of example, the agent may be abrin-A chain, ricin A-chain, immunotoxins, chemotherapy drugs, and $^{131}$I and $^{90}$Y radionuclides, among others.

Having now generally described this invention, the same will be better understood by reference to certain specific examples, which are included herein for purposes of illustration only and are not intended to be limiting of the invention or any embodiment thereof, unless so specified.

EXAMPLES

Example 1
Immunoscreening λgt11 cDNA library

Two human breast cDNA libraries were purchased from Clontech (Palo Alto, Calif.). The first library was originally prepared from RNA extracted from adult breast tissue excised during mastectomy obtained during the 8th month of pregnancy and showing well-differentiated tissue and lactational competence. The other cDNA library, ZR75, was reverse transcribed from mRNA extracted from the breast carcinoma cell line ZR75. The oligo-dT primed cDNA from this tissue was inserted into the Eco R1 site of λgt11. Plating and screening of the library with monoclonal antibodies was done essentially as described by Young and Davis (Young, R. A. and Davis, R. W., PNAS (U.S.A) 80:1194–1198 (1983)). The library was screened with a cocktail of monoclonal antibodies Mc3, Mc8, Mc15 and Mc16 all of which bind the 46 Kdalton component of human milk fat globule. (Peterson et al, Hybridoma (1990), supra; Larocca et al, Cancer Res. 51:4994 (1991)).

Example 2
Blot Analysis

The cell lines were grown to late log phase and total cell RNA prepared by the method of Chirgwin et al. (Chirgwin, J. M., Przybyla, A. E., MacDonald, R. J., and Rutter, W. J. Biochemistry 18:5294–5299. (1979)). RNA was glyoxalated, electrophoresed, and blotted according to Thomas (Thomas, P., "Hybridization of denatured RNA and small DNA fragments transferred to nitrocellulose", PNAS (USA) 77:5201–5205 (1980)) and RNA bound to nylon (Biodyne) filters using UV irradiation.

Single stranded RNA probes were made in vitro using SP6 and T7 RNA polymerase according to manufacturer (Promega) and labelled by incorporation of $^{32}$P-UTP at 800 Ci/mmol (Amersham). Hybridization of RNA probes to RNA blots was at 70° C., 0.1×SSC, 0.1% SDS. Blots were exposed to X-ray film (Kodak X-AR) at –80° C. with intensifying screens.

Example 3
DNA Sequencing

Large scale bacteriophage DNA preparations were made from phage lysates, and the Eco R1 digested cDNA insert subcloned into pGEM3 (Promega, Madison, Wis.) according to standard protocols (Sambrook, J., Fritsch, D., and Maniatis, T., in Molecular Cloning: A Laboratory Manual/Second edition, Cold Spring Harbor Laboratory Press, Cold Spring Harbor, N.Y. (1990)). Dideoxy sequencing of the insert in pGEM3 was done with a modified T7 DNA polymerase (Sequenase) directly on the plasmid DNA using T7 or SP6 promoter sequence primers (Promega) according to the manufacturer's protocol (USB, Cleveland, Ohio). The sequence was confirmed by repeatedly sequencing both strands of the insert.

Example 4
Results 15 positive plaques were selected after screening about 1×10$^6$ plaques from λgt11 lactating breast cDNA library. The largest cDNA, BA46-1 was 1271 base pairs long. A series of positive λgt11 clones were used to lysogenize Y1089 and the resulting fusion protein containing induced cell extracts were analyzed by dot blot analysis for reactivity with each of the monoclonal antibodies contained in the screening cocktail.

It was found that monoclonal antibodies Mc8, Mc15 and Mc16 bound to all the positive λgt11 lysogen extracts but not to the control λgt11 extract (not shown). Monoclonal antibody Mc3, however, did not bind any of the lysates indicating that its epitope requires either glycosylation, or secondary structure, or is not present in the library.

Example 5
Partial RNA Sequence

Single stranded RNA probes representing each strand of the BA46-1 cDNA insert were prepared by subcloning into Gem3 and transcribing in vitro with T7 or SP6 polymerase.

Several neoplastic tumor cell lines were studied including 5 breast lines and a lymphoid cell line of carcinomic origin for BA46-1 specific RNA. As shown in FIG. 1 accompanying this patent, a single 2.2 kb RNA was detected in all cell lines tested. This RNA is also detectable in the Raji cell line, but at a much lower level that requires longer exposures and it, therefore, does not appear in FIG. 1.

There was considerable variation in the observed expression levels of the 2.2 kb RNA that were detected in the different cell lines. The lung (A549), ovary (SKOV3) and two breast (E11-G and HS578T) carcinoma cell lines accumulated from 10–50 fold more transcript than the other cell lines.

Example 6

Specificity Studies

Although the antibodies used to select the cDNA bound only to breast carcinomas by immunohistochemistry (Peterson et al, Hybridoma (1990), supra), expression of the 2.2 kb RNA fragment that encodes the 46 Kdalton HMFG antigen is expressed in many different cancer cell lines, such as carcinoma cell lines. The broad specificity found for cancers from tissues of different origins, not only breast neoplastic cells may be attributed to a deregulation of this gene in neoplastic tumors such as carcinomas but not in normal tissue. Normal epithelial tissue may also express the 46 Kdalton app. MW HMFG protein, but process it in a way that blocks the epitopes that are exposed in the breast cell version of the protein by, for example, producing alterations in its glycosylation. The high molecular weight mucin-like protein of HMFG is also expressed in non-breast cancer cells such as carcinoma cells, but its altered processing in the pancreas, for example, leads to the exposure of different antigenic sites than in the breast (Lan, M. S., Hollingworth, M. A., and Metzgar, T. S., Cancer Res. 50:2997 (1990)).

Example 7

Partial DNA Sequence

The nucleotide and derived amino acid sequence of BA46-1 cDNA is shown in Table 1 below.

TABLE 1

Partial DNA Sequence and Deduced Amino Acid Sequence of 46 Kdalton HMFG Antigen

| | * | | 10 | * | | 20 | | * | | 30 | | * | | 40 |
|---|---|---|---|---|---|---|---|---|---|---|---|---|---|---|
| GAT | TTC | ATC | CAT | GAT | GTT | AAT | AAA | AAA | CAC | AAG | GAG | TTT | GTG |
| Asp | Phe | Ile | His | Asp | Val | Asn | Lys | Lys | His | Lys | Glu | Phe | Val |
| * | | 50 | | * | | 60 | | * | | 70 | | * | | 80 |
| GGT | AAC | TGG | AAC | AAA | AAC | GCG | GTG | CAT | GTC | AAC | CTG | TTT | GAG |
| Gly | Asn | Trp | Asn | Lys | Asn | Ala | Val | His | Val | Asn | Leu | Phe | Glu |
| * | | 90 | | * | | 100 | | * | | 110 | | * | | 120 | * |
| ACC | CCT | GTG | GAG | GCT | CAG | TAC | GTG | AGA | TTG | TAC | CCC | ACG | AGC |
| Thr | Pro | Val | Glu | Ala | Gln | Tyr | Val | Arg | Leu | Tyr | Pro | Thr | Ser |
| | | 130 | | * | | 140 | | * | | 150 | | * | | 160 | * |
| TGC | CAC | ACG | GCC | TGC | ACT | CTG | TTT | GAG | CTA | CTG | CCG | GGC | TGT |
| Cys | His | Yhr | Ala | Cys | Thr | Leu | Arg | Phe | Glu | Leu | Leu | Gly | Cys |
| 170 | | * | 180 | | * | | 190 | * | | 200 | | * | | 210 |
| GAG | CTG | AAC | GGA | TGC | GCC | AAT | CCC | CTG | GGC | CTG | AAG | AAT | AAC |
| Glu | Leu | Asn | Gly | Cys | Ala | Asn | Pro | Leu | Gly | Leu | Lys | Asn | Asn |
| | * | | 220 | * | | 230 | | * | | 240 | | * | | 250 |
| AGC | ATC | CCT | GAC | AAG | CAG | ATC | ACG | GCC | TCC | AGC | AGC | TAC | AAG |
| Ser | Ile | Pro | Asp | Lys | Gln | Ile | Thr | Ala | Ser | Ser | Ser | Tyr | Lys |
| * | | | 260 | | * | | 270 | | * | | 280 | | * | | 290 |
| ACC | TGG | GGC | TTG | CAT | CTC | TTC | AGC | TGG | AAC | CCC | TCC | TAT | GCA |
| Thr | Trp | Gly | Leu | His | Leu | Phe | Ser | Trp | Asn | Pro | Ser | Tyr | Ala |
| * | | 300 | | * | | 310 | * | | 320 | | * | | 330 | * |
| CGG | CTG | GAC | AAG | CAG | GGC | AAC | TTC | AAC | GCC | TGG | GTT | GCG | GGG |
| Arg | Leu | Asp | Lys | Gln | Gly | Asn | Phe | Asn | Ala | Trp | Val | Ala | Gly |
| | | 340 | * | | 350 | | * | | 360 | | * | | 370 | * |
| AGC | TAC | GGT | AAC | GAT | CAG | TGG | CTG | CAG | GTG | GAC | CTG | GGC | TCC |
| Ser | Tyr | Gly | Asn | Asp | Gln | Trp | Leu | Gln | Val | Asp | Leu | Gly | Ser |
| 380 | | * | 390 | | * | | 400 | * | | 410 | | * | | 420 |
| TGC | AAG | GAG | GTG | ACA | GGC | ATC | ATC | ACC | CAG | GGG | GCC | CGT | AAC |
| Ser | Lys | Glu | Val | Thr | Gly | Ile | Ile | Thr | Gln | Gly | Ala | Arg | Asn |
| | * | | 430 | | * | | 440 | | * | | 450 | | * | | 460 |
| TTT | GGC | TCT | GTC | CAG | TTT | GTG | GCA | TCC | TAC | AAG | GTT | GCC | TAC |
| Phe | Gly | Ser | Val | Gln | Phe | Val | Ala | Ser | Tyr | Lys | Val | Ala | Tyr |
| * | | 470 | | * | | 480 | | * | | 490 | | * | | 500 |
| AGT | AAT | GAC | AGT | GCG | AAC | TGG | ACT | GAG | TAC | CAG | GAC | CCC | AGG |
| Ser | Asn | Asp | Ser | Ala | Asn | Trp | Thr | Glu | Tyr | Gln | Asp | Pro | Arg |
| * | | 510 | | * | | 520 | * | | 530 | | * | | 540 | * |
| ACT | GGC | AGC | AGT | AAG | ATC | TTC | CCT | GGC | AAC | TGG | GAC | AAC | CAC |
| Thr | Gly | Ser | Ser | Lys | Ile | Phe | Pro | Gly | Asn | Trp | Asp | Asn | His |
| | | 550 | * | | 560 | | * | | 570 | | * | | 580 | * |
| TCC | CAC | AAG | AAG | AAC | TTG | TTT | GAG | ACG | CCC | ATC | CTG | GCT | CGC |
| Ser | His | Lys | Lys | Asn | Leu | Phe | Glu | Thr | Pro | Ile | Leu | Ala | Arg |
| 590 | | * | 600 | | * | | 610 | * | | 620 | | * | | 630 |
| TAT | GTG | CGC | ATC | CTG | CCT | GTA | GCC | TGG | CAC | AAC | CGC | ATC | GCC |
| Tyr | Val | Arg | Ile | Leu | Pro | Val | Ala | Trp | His | Asn | Arg | Ile | Ala |
| | * | | 640 | * | | 650 | | * | | 660 | | * | | 670 |
| CTG | CGC | CTG | GAG | CTG | CTG | GGC | TGT | TAG | TGG | CCA | CCT | GCC | ACC |
| Leu | Arg | Leu | Glu | Leu | Leu | Gly | Cys | End | (■) | | | | |
| * | | 680 | | * | | 690 | | * | | 700 | | * | | 710 |
| CCC | AGG | TCT | TCC | TGC | TTT | CCA | TGG | GCC | CGC | TGC | CTC | TTG | GCT |

TABLE 1-continued

Partial DNA Sequence and Deduced Amino Acid Sequence of 46 Kdalton HMFG Antigen

```
*       720     *               730     *               740     *       750             *
TCT     CAG     CCC     CTT     TAA     ATC     ACC     ATA     GGG     CTG     GGG     ACT     GGG     GAA
        760     *               770             *       780             *               790     *
GGG     GAG     GGT     GTT     CAG     AGG     CAG     CAC     CAC     CAC     ACA     GTC     ACC     CCT
800             *       810             *               820     *               830             *       840
CCC     TCC     CTC     TTT     CCC     ACC     CTC     CAC     CTC     TCA     CGG     GCC     CTG     CCC
        *               850     *               860             *       870             *               880
CAG     CCC     CTA     AGC     CCC     GTC     CCC     TAA     CCC     CCA     GTC     CTC     ACT     GTC
*               890             *       900             *               910     *               920
CTG     TTT     TCT     TAG     GCA     CTG     AGG     GAT     CTG     AGT     AGG     TCT     GGG     ATG
*       930             *               940     *               950             *       960             *
GAC     AGG     AAA     GGG     CAA     AGT     AGG     GCG     TGT     GGT     TTC     CCT     GCC     CCT
        970     *               980             *       990             *               1000    *
GTC     CGG     ACC     GCC     GAT     CCC     AGG     TGC     GTG     TGT     CTC     TGT     CTC     TCC
1010            *       1020            *               1030    *               1040            *       1050
TAG     CCC     CTC     TCT     CAC     ACA     TCA     CAT     TCC     CAT     GGT     GGC     CTC     AAG
        *               1060    *               1070            *       1080            *               1090
AAA     GGC     CCG     GAA     GCC     CCA     GGC     TGG     AGA     TAA     CAG     CCT     CTT     GCC
*               1100            *       1110            *               1120    *               1130
CGT     CGG     CCC     TGC     GTC     GGC     CCT     GGG     GTA     CCA     TGT     GCC     ACA     ACT
*       1140            *               1150    *               1160            *       1170            *
GCT     GTG     GCC     CCC     TGT     CCC     CAA     GAC     ACT     TCC     CCT     TGT     CTC     CCT
        1180    *               1190            *       1200            *               1210    *
GGT     TGC     CTC     TCT     TGC     CCC     TTG     TCC     TGA     AGC     CCA     GCG     ACA     CAG
1220            *       1230            *               1240    *               1250            *       1260
AAG     GGG     GTG     GGG     CGG     GTC     TAT     GGG     GAG     AAA     GGG     AGC     GAG     GTC
        *               1270    *               1280            *       1290            *               1300
AGA     GGA     GGG     CAT     GGG     TTG     GCA     GGG     TGG     GCG     TTT     GGG     GCC     CTC
*               1310            *       1320            *               1330    *               1340
ATG     CTG     GCT     TTT     CAC     CCC     AGA     GGA     CAC     AGG     CAG     CTT     CCA     AAA
*       1350            *               1360    *               1370            *       1380
TAT     ATT     TAT     CTT     CTT     CAC     GGG     AAA     AAA     AAA     AAA     AAA     ACC     G (□)
```

(□): SEQ. ID. No. 1
(■): SEQ. ID. No. 2
Potential n-linked glycosylation sites are underlined The partial ORF sequence is 217 amino acids long and compounds to a theoretical molecular weight of about 24 Kdalton, representing the C-terminus of the complete protein. There are four potential sites for n-linked glycosylation and the polypeptide sequence is asparagine and leucine rich.

Example 8
Homology to Clotting Factors

A comparison of the nucleotide sequence to the EMBL database using FSTNSCAN (PCGENE) revealed extended homology with human serum factors V and VIII and protein C. The partial deduced protein sequence, however, shares identity only with factors V and VIII but not with protein C since the homology at the nucleotide level is found in an intervening sequence (See, Table 2 below).

TABLE 2

Comparison of Deduced BA46-1 Amino Acid Sequence with C-terminal Human Serum Factors V and VIII

| 46 Kdalton | F | I | H | D | V | N | K | K | H | K | E | F | V | G | N | W | N | K | N | A | V | H | V | N |   |
|---|---|---|---|---|---|---|---|---|---|---|---|---|---|---|---|---|---|---|---|---|---|---|---|---|---|
| FAV | F | K | G | N | S | T | R | N | V | M | Y | F | N | G | N | S | D | A | S | T | I | K | E | N |   |
| FAVIII | Y | R | G | N | S | T | G | T | L | M | V | F | F | G | N | V | D | S | S | G | I | K | H | N |   |
|  | L | F | E | T | P | V | E | A | Q | Y | V | R | L | Y | P | T | S | C | H | T | A | C | T | L | R | F | E | L |
|  | Q | F | D | P | P | I | V | A | R | Y | I | R | I | S | P | T | R | A | Y | N | R | P | T | L | R | L | E | L |
|  | I | F | N | P | P | I | I | A | R | Y | I | R | L | H | P | T | H | Y | S | I | R | S | T | L | R | M | E | L |
|  | L | G | C | E | L | N | G | C | A | N | P | L | G | L | K | N | N | S | I | P | D | K | Q | I | T | A | S | S |
|  | Q | G | C | E | V | N | G | C | S | T | P | L | G | M | E | N | G | K | I | E | N | K | Q | I | T | A | S | S |
|  | M | G | C | D | L | N | S | C | S | M | P | L | G | M | E | S | K | A | I | S | D | A | Q | I | T | A | S | S |
|  | S | Y | K | T | W | G | L | H | L | F | S | W | N | P | S | Y | A | R | L | D | K | Q | G | N | F | N | A | W |
|  | F | K | K | S | W | W | G | D | Y | — | — | W | E | P | F | R | A | R | L | N | A | Q | G | R | V | N | A | W |
|  | Y | F | T | N | M | F | A | T | — | — | — | W | S | P | S | K | A | R | L | H | L | Q | G | R | S | N | A | W |
|  | V | A | G | S | Y | G | N | D | Q | W | L | Q | V | D | L | G | S | S | K | E | V | T | G | I | I | T | Q | G |
|  | Q | A | K | A | N | N | N | K | Q | W | L | E | I | D | L | L | K | I | K | K | I | T | A | I | I | T | Q | G |
|  | R | P | Q | V | N | N | P | K | E | W | L | Q | V | D | F | Q | K | T | M | K | V | T | G | V | T | T | Q | G |
|  | A | R | N | F | G | S | V | Q | F | V | A | S | Y | K | V | A | Y | S | N | D | S | A | N | W | T | E | Y | Q |
|  | C | K | S | L | S | S | E | M | Y | V | K | S | Y | T | I | H | Y | S | E | Q | G | V | E | W | K | P | Y | R |
|  | V | K | S | L | L | T | E | M | Y | V | K | E | F | L | I | S | S | S | Q | D | G | H | Q | W | T | L | F | F |
|  | D | P | R | T | G | S | S | S | K | I | F | P | G | N | W | D | N | H | S | H | K | K | N | L | F | E | T | P | I |

TABLE 2-continued

Comparison of Deduced BA46-1 Amino Acid Sequence
with C-terminal Human Serum Factors V and VIII

| L | K | S | S | M | V | D | K | I | F | E | G | N | T | N | T | K | G | H | V | K | N | F | F | N | P | P | I |   |
| Q | N | — | — | G | K | V | K | V | F | Q | G | N | Q | D | S | F | T | P | V | V | N | S | L | D | P | P | L |   |
| L | A | R | Y | V | R | I | L | P | V | A | W | H | N | R | I | A | L | R | L | E | L | L | G | C |   |   |   |   |
| I | S | R | F | I | R | V | I | P | K | T | W | N | Q | S | I | A | L | R | L | E | L | F | G | C | D | — | — |   |
| L | T | R | Y | L | R | I | H | P | Q | S | W | V | H | Q | I | A | L | R | M | E | V | L | G | C | E | A | Q |   |
|   |   |   |   | (SEQ. ID. No. 3) |
| — | I | Y |   | (SEQ. ID. No. 4) |
| D | L | Y |   | (SEQ. ID. No. 5) |

An arrow indicates function of C1 and C2 repeats

There is about 43% identity of BA46 to Factor V and about 38% to factor VIII. The region of factors V and VIII in Table 2 share about 47% identity.

Example 9
Amino Acid Sequence

The analysis of the derived amino acid sequence of the 46 Kdalton app. MW protein is consistent with its description as a glycosylated protein containing four N-linked glycosylation sites. Since the 46 Kdalton app. MW protein has homology to both factors V and VIII, there may be a common ancestral protein to these serum clotting factors. The homology is in the C1C2 region of the light chain of factor VIII (Arai, M., Scandella, D., and Hoyer, L. W., J. Clin. Invest. 83:1978–1984 (1989)).

Arai et al have shown that human antibodies that bind the C1C2 region of the light chain from hemophiliacs treated with factor VIII inhibit factor VIII by preventing the interaction of factor VIII with phospholipids and that it is implicated in phospholipid binding. It is likely that the similar sequence is also important for phospholipid binding in the 46 Kdalton glycoprotein.

The C-terminal portion could serve as a novel "anchor" sequence for the 46 Kdalton app. MW protein or it could be involved in the binding of the mucin/membrane to the phospholipids on the surface of the growing milk fat droplet (Long, C. A., and Patton, S., J. Dairy Sci. 61:1392–1399 (1978)). It could also be involved in the assembly of the mucin complex at the plasma membrane surface.

Example 10
Screening of cDNA Libraries

The ZR75 λgt11 cDNA library was screened using an isolated cloned LB21 sequence encompassing bases 562 through 1838 of the total 1934 base pairs of the 46 Kdalton app. MW BA46 clone and labeled with $P^{32}$ using random primers. The cDNA clone LB21 utilized herein comprises a portion of the C-terminal region of the BA46 cDNA, and its cloning and expression in E. coli as an expression vector (pEX/LB21) have been described by Larocca, et al (Larocca et al, Molecular Cloning and Expression of Breast Mucin-associated Antigens", in Breast Epithelial Antigens: Molecular Biology to Clinical Applications, Ceriani R. L. Ed., PP. 35–44, New York Plenum Press (1991)). The bacteriophages were plated at a density of 30,000 pfu/150 mm plates with E. coli Y1090, and blotted with nitrocellulose filters as described by Larocca et al. (Larocca et al, "Cloning and sequencing of a complementary DNA encoding a Mr 70,000 human breast epithelial mucin-associated antigen", Cancer Res. 50:5925–5930 (1990)). The $P^{32}$-labeled LB21 clones were then screened, and positive plaques visualized by autoradiography, picked and plaque purified. The inserts were amplified by PCR using forward and reverse primers for the adjacent λgt11 bacteriophage sequences, subcloned into pGEM3 (Promega, Madison, Wis.) at the EcoR1 site, and sequenced by the Sanger method of dideoxynucleotide chain termination as described by Larocca et al, "Cloning and sequencing of a complementary DNA encoding a Mr 70,000 human breast epithelial mucin-associated antigen", (Cancer Res.50:5925–5930 (1990); Sanger et al, "DNA sequencing with chain-terminating inhibitors", PNAS (USA) 74:463–5467 (1977)). The screening of the human breast λgt11 cDNA library was done by PCR using an up-stream primer for the λgt11 vector and several downstream primers for known sequences in the 5' region.

Example 11
PCR Primer Synthesis

The primers listed in Table 3 below were synthesized for the PCR using an Applied Biosystems model 391 PCR-MATE DNA synthesizer by the phosphoramidite method. The oligonucleotides were run on a 8M urea/10% polyacrylamide denaturing gel to assess their purity and integrity.

TABLE 3

DNA Sequence of Primers Utilized

| Primer | Type[+] | DNA Sequence |
|---|---|---|
| 5'-46KRT[*] | Antisense | 5'-GGTGTCCAGGCATTGACCAT-3' |
| BA46 P-2[□] | Antisense | 5'-GCTGCAAACCCAAGAAGGTCAC-3' |
| BA46 P-A[†] | Antisense | 5'-TAAGGCACGTGCAGGTGTACGA-3' |
| BA46P-C[°] | Antisense | 5'-TTGGAACAGATATCCAGGGCGA-3' |
| λgt11 Fwd. | Sense | 5'-GGTGGCGACGACTCCTGGAGCCCG-3' |
| λgt11 Rev. | Sense | 5'-TTGACACCAGACCAACTGGTAATG-3' |

[+]Sense or antisense indicates the sequence of the primer is either identical or complementary to the BA46 mRNA, respectively.
[*]Bases 337–356 of the M, 46,000 gene coding sequence.
[□]Bases 277–298 of the M, 46,000 gene coding sequence.
[†]Bases 154–175 of the M, 46,000 gene coding sequence.
[°]Bases 65–86 of the M, 46,000 gene coding sequence.

Example 12
PCR Conditions

The PCR was carried out in a 50 ml reaction volume using the GeneAmp PCR kit (Perkin Elmer Cetus, Conn.). The samples were run under "hot start" conditions, in 0.2 ml PCR MicroAmp™ tubes using the GeneAmp™ PCR system 9600 (Perkin Elmer-Cetus, Conn.). The following conditions were used for PCR screening of the human breast cDNA library. In each tube, 5 μl of a 1:10 dilution of the cDNA library (equivalent to approximately $0.65 \times 10^6$ independent cell clones) were added to 40 μl PCR master reaction mixture containing 5 μl of 10×PCR buffer II (100 mM Tris-HCl, pH 8.3, 500 mM KCl), 4 μl of 25 mM $MgCl_2$ 1 μl each of 10 mM dNTP, 17 μl sterile water, 5 μl of 2 mM ($M_o$=46,000) gene specific antisense primer, and 5 μl of 2 mM λgt11 sense primer. The samples were heated to 95° C. for 2 min in the PCR system 9600, allowed to cool to 75° C. and held at this temperature while 1.25 units of "AmpliTaq" DNA polymerase were added in 5 μl of 1×Taq buffer. Primer annealing was initially performed at 62° C. for 30 sec followed by 35 cycles of denaturation at 95° C., ramping to 64° C. in 30 sec and annealing and extending at 64° C. for 30 sec. After completion of the PCR cycles, the reaction mixtures were extended at 72° C. for 7 min and cooled to 4° C.

The amplified DNA was subjected to gel electrophoresis, ethidium bromide stained, and visualized under UV light. A smear of DNA bands relating to incomplete 5'-ends of the BA46 cDNA was cloned directly into pCR™ II using a TA cloning kit from Invitrogen (San Diego, Calif.). This method took advantage of the non-template dependent activity of Taq polymerase that adds a single dA to the 3' end of PCR duplex products (Marchuck et al, "Nucleic Acids Res. 19:1154 (1991)). Single 3'dT overhangs in the vector, PCR™ II, allowed for PCR product insertion.

Example 13
Nucleotide Sequencing

The cDNA clones isolated from the screening of the ZR75 breast cell λgt11 cDNA library were subcloned into a pGEM3 plasmid and sequenced by the didioxynucleotide chain termination method as described by Larocca et al. (Larocca, et al, "Cloning and sequencing of a complementary DNA encoding a M 70,000 human breast epithelial mucin-associated antigen", Cancer Res. 50:5925 (1990)). Positive clones obtained from the human breast library by the PCR method were picked, amplified and phage DNA isolated by the method of lysis by boiling as described by Sambrook et al. (Sambrook et al, in Molecular Cloning: A Laboratory Manual, Cold Spring Harbor, Cold Spring Harbor Press (1989)). EcoR1 digested inserts were screened by gel electrophoresis choosing DNA fragments of the size expected. The size of the chosen DNA fragments was assessed from the fact that a single 2.2 kilobase RNA was detected in carcinoma cell lines, by Northern blotting as described above (Larocca et al., "A 46 Kdalton human milk fat globule glycoprotein that is highly expressed in carcinoma cells has homology with human clotting factors V and VIII", Cancer Res. 51:4994 (1991)).

High yields of pure supercoiled plasmid DNA for sequencing were prepared from overnight cultures of selected clones using the Qiagen plasmid minipreparation kit (Qiagen Inc., Calif.). The insert in pCR™ II was sequenced by the method of dideoxynucleotide chain termination (Sanger, supra), using a modified T7 DNA polymerase (Sequenase Version 2.0) under the conditions recommended by the supplier (USB Corp., Cleveland, Ohio). Both strands were sequenced by priming in the plasmid with either M13 reverse or M13 (−40) forward primers (USB Corp., Ohio). The analysis of the sequence was performed using GeneWorks software (IntelliGenetics, Inc., Mountain View, Calif.).

The breast cDNA library was screened by PCR, priming with the λgt11 Fwd. and the BA46 P-2 primers described above. The latter primer comprises bases 277–298, 37 bases within the 5' end of the sequence obtained by screening the ZR75 library and provided an extra 197 bases of the 5' end of the $M_r$=46,000 cDNA. A second BA46 gene specific primer (BA46 P-A, bases 154–175) was synthesized within the extended 5' end sequence and used to further screen the breast cDNA library. The BA46 cDNA was further extended by 43 bases including the start codon.

Example 14
Confirmation of 5' End of BA 46 cDNA

The 5'-end of the 46 Kdalton BA46 cDNA was confirmed by screening mRNA from a breast cell line using the 5'-AmpliFinder RACE kit (Clonetech, Palo Alto). PolyA$^+$ RNA was prepared from the "ELL-G" breast cell line using "FastTrack mRNA isolation kit, version 3.2" (Invitrogen, San Diego, Calif.). cDNA was synthesized from 2 μg of the ELL-G mRNA using the antisense gene specific primer "5'-46KRT" (bases 337–356) with the 5'-AmpliFinder RACE kit. The RNA template was then hydrolyzed with NaOH, and the cDNA purified by binding to a glass matrix support (GENO-BIND™ particles) in preparation for the ligation of a single stranded anchor oligonucleotide to the 3' end of the cDNA.

The gene was then amplified by PCR using the nested antisense gene-specific primers "BA46 P-A and BA46 P-C" and a primer complementary to the anchor. PCR was carried out as described above under "hot start" conditions using AmpliTaq DNA polymerase, Stoffel fragment (Perkin Elmer-Cetus). Each 50 μl of PCR reaction mixture contained a 1:100 dilution of the anchor ligation mix, 1×Stoffel buffer (10 mM KCl, 10 mM Tris HCl, pH 8.3), 3 mM MgCl$_2$, 0.2 mM each of dNTP and 0.3 μM of sense and antisense (both) primers.

The samples were heated to 98° C. for 1 min, cooled to 75° C., and 5 units of the Stoffel fragment added. The primers were initially annealed and extended at 64° C. for 30 seconds. Two PCR methods were used to amplify the gene. The first consisted of 10 cycles of denaturing at 97° C. for 10 seconds and annealing and extending at 62° C. for 25 seconds. This was followed by 30 cycles of denaturing at 95° C. for 10 seconds and annealing and extending at 60° C. for 25 seconds. A final extension at 72° C. for 7 min ensured that all the templates were completed. The PCR products were visualized on a 2% agarose gel, and then cloned into the pCR II vector (TA cloning kit, Invitrogen) for dideoxynucleotide sequencing.

Example 15
Complete DNA Sequence of Polynucleotide Encoding 46 Kdalton HMFG Antigen The partial cDNA sequence for the 46 Kdalton HMFG antigen clone (BA46) provided in Example 7 above was completed. A complete DNA sequence was obtained by screening and PCR amplication of a cDNA library, and the rapid amplification of cDNA ends (RACE) method. The breast carcinoma cell line ZR75 cDNA library was screened with the partial cDNA clone LB21 of the BA46 sequence shown above, and labeled with P$^{32}$.

Two new cDNA clones were isolated, which provided further information cDNA segment encoding the 46 Kdalton HMFG antigen. These two completed the 3' end (97 bases to the polyadenylation site), and extended by 267 bases the 5' end of the cDNA sequence.

The sequence of the 5' end of the cDNA was completed by screening a human breast λgt11 cDNA by PCR amplification using antisense primers on end of the BA46 cDNA, and sense primers within the λgt11 cloning vector. The latter PCR method allowed the complete sequencing of the open reading frame (ORF) of the 46 Kdalton HMFG polypeptide (BA46) cDNA. The ORF sequence was confirmed and the non-coding 5'end was sequenced by the method. Each cDNA insert was sequenced in both directions on at least two independent isolates to verify the sequence.

The entire cDNA contains 1934 bases and an ORF 1161 nucleotides encoding 387 nucleotides as shown in Table 4 below.

TABLE 4

Complete DNA Sequence Encoding the 46 Kdalton
HMFG Antigen & Deduced Amino Acid Sequence

```
   1 AGAACCCCGCGGGGTCTGAGCAGCCCAGCGTGCCCATTCCAGCGCCCGCGTCCCCGCAGC
  61 ATGCCGCGCCCCCGCCTGCTGGCCGCGCTGTGCGGCGCGCTGCTCTGCGCCCCAGCCTC
   1  M   P   R   P   R   L   L   A   A   L   C   G   A   L    L    C    A    P    S    L
 121 CTCGTCGCCCTGGATATCTGTTCCAAAAACCCCTGCCACAACGGTGGTTTATGCGAGGAG
  21  L   V   A   L   D   I   C   S   K   N   P   C   H   N    G    G    L    C    E    E
 181 ATTTCCCAAGAAGTGCGAGGAGATGTCTTCCCCTCGTACACCTGCACGTGCCTTAAGGGC
  41  I   S   Q   E   V   R   G   D   V   F   P   S   Y   T    C    T    C    L    K    G
 241 TACGCGGGCAACCACTGTGAGACGAAATGTGTCGAGCCACTGGGCATGGAGAATGGGAAC
  61  Y   A   G   N   H   C   E   T   K   C   V   E   P   L    G    M    E    N    G    N
 301 ATTGCCAACTCACAGATCGCCGCCTCATCTGTGCGTGTGACCTTCTTGGGTTTGCAGCAT
  81  I   A   N   S   Q   I   A   A   S   S   V   R   V   T    F    L    G    L    Q    H
 361 TGGGTCCCGGAGCTGGCCCGCCTGAACCGCGCAGGCATGGTCAATGCCTGGACACCCAGC
 101  W   V   P   E   L   A   R   L   N   R   A   G   M   V    N    A    W    T    P    S
 421 AGCAATGACGATAACCCCTGGATCCAGGTGAACCTGCTGCGGAGGATGTGGGTAACAGGT
 121  S   N   D   D   N   P   W   I   Q   V   N   L   L   R    R    M    W    V    T    G
 481 GTGGTGACGCAGGGTGCCAGCCGCTTGGCCAGTCATGAGTACCTGAAGGCCTTCAAGGTG
 141  V   V   T   Q   G   A   S   R   L   A   S   H   E   Y    L    K    A    F    K    V
 541 GCCTACAGCCTTAATGGACACGAATTCGATTTCATCCATGATGTTAATAAAAAACACAAG
 161  A   Y   S   L   N   G   H   E   F   D   F   I   H   D    V    N    K    K    H    K
 601 GAGTTTGTGGGTAACTGGAACAAAAACGCGGTGCATGTCAACCTGTTTGAGACCCCTGTG
 181  E   F   V   G   N   W   N   K   N   A   V   H   V   N    L    F    E    T    P    V
 661 GAGGCTCAGTACGTGAGATTGTACCCCACGAGCTGCCACACGGCCTGCACTCTGCGCTTT
 201  E   A   Q   Y   V   R   L   Y   P   T   S   C   H   T    A    C    T    L    R    F
 721 GAGCTACTGGGCTGTGAGCTGAACGGATGCGCCAATCCCCTGGGCCTGAAGAATAACAGC
 221  E   L   L   G   C   E   L   N   G   C   A   N   P   L    G    L    K    N    N    S
 781 ATCCCTGACAAGCAGATCACGGCCTCCAGCAGCTACAAGACCTGGGGCTTGCATCTCTTC
 241  I   P   D   K   Q   I   T   A   S   S   S   Y   K   T    W    G    L    H    L    F
 841 AGCTGGAACCCCTCCTATGCACGGCTGGACAAGCAGGGCAACTTCAACGCCTGGGTTGCG
 261  S   W   N   P   S   Y   A   R   L   D   K   Q   G   N    F    N    A    W    V    A
 901 GGGAGCTACGGTAACGATCAGTGGCTGCAGGTGGACCTGGGCTCCTCGAAGGAGGTGACA
 281  G   S   Y   G   N   D   Q   W   L   Q   V   D   L   G    S    S    K    E    V    T
 961 GGCATCATCACCCAGGGGGCCCGTAACTTTGGCTCTGTCCAGTTTGTGGCATCCTACAAG
 301  G   I   I   T   Q   G   A   R   N   F   G   S   V   Q    F    V    A    S    Y    K
1021 GTTGCCTACAGTAATGACAGTGCGAACTGGACTGAGTACCAGGACCCCAGGACTGGCAGC
 321  V   A   Y   S   N   D   S   A   N   W   T   E   Y   Q    D    P    R    T    G    S
1081 AGTAAGATCTTCCCTGGCAACTGGGACAACCACTCCCACAAGAAGAACTTGTTTGAGACG
 341  S   K   I   F   P   G   N   W   D   N   H   S   H   K    K    N    L    F    E    T
1141 CCCATCCTGGCTCGCTATGTGCGCATCCTGCCTGTAGCCTGGCACAACCGCATCGCCCTG
 361  P   I   L   A   R   Y   V   R   I   L   P   V   A   W    H    N    R    I    A    L
1201 CGCCTGGAGCTGCTGGGCTGTTAGTGGCCACCTGCCACCCCCAGGTCTTCCTGCTTTCCA
 381  R   L   E   L   L   G   C      (SED. ID No: 6)
1261 TGGGCCCGCTGCCTCTTGGCTTCTCAGCCCCTTTAAATCACCATAGGGCTGGGGACTGGG
1321 GAAGGGGAGGGTGTTCAGAGGCAGCACCACCACACAGTCACCCCTCCCTCCCTCTTTCCC
1381 ACCCTCCACCTCTCACGGGCCCTGCCCCAGCCCCTAAGCCCCGTCCCCTAACCCCCAGTC
1441 CTCACTGTCCTGTTTTCTTAGGCACTGAGGGATCTGAGTAGGTCTGGGATGGACAGGAAA
1501 GGGCAAAGTAGGGCGTGTGGTTTCCCTGCCCCTGTCCGGACCGCCGATCCCAGGTGCGTG
1561 TGTCTCTGTCTCTCCTAGCCCCTCTCTCACACATCACATTCCCATGGTGGCCTCAAGAAA
1621 GGCCCGGAAGCCCCAGGCTGGAGATAACAGCCTCTTGCCCGTCGGCCCTGCGTCGGCCCT
1681 GGGGTACCATGTGCCACAACTGCTGTGGCCCCCTGTCCCCAAGACACTTCCCCTTGTCTC
1741 CCTGGTTGCCTCTCTTGCCCCTTGTCCTGAAGCCCAGCGACACAGAAGGGGGTGGGGCGG
1801 GTCTATGGGGAGAAAGGGAGCGAGGTCAGAGGAGCCGGCATGGGTTGGCAGGGTGGGCGT
1861 TTGGGGCCCTCATGCTGGCTTTTCACCCCAGAGGACACAGGCAGCTTCCAAAATATATTT
1921 ATCTTCTTCACGGG (SED. ID No: 7)
```

Example 16
Characteristics of BA46 DNA Segment

The cDNA sequence is characterized by a 3' poly(A) tail and an untranslated 3' region of 713 nucleotides. The usual consensus polyadenylation signal sequence of AATAAA is not found but the sequence AATATA is found in the same position relative to the AATACA sequence found in the mouse MFGE8 cDNA sequence, 17 nucleotides upstream of the poly(A) tail (Stubbs et al., "cDNA cloning of a mouse mammary epithelial cell surface protein reveals the existence of epidermal growth factor-like domains linked to factor VIII-like sequences", PNAS (USA) 87:8417–8421 (1990)). The AATACA and AATATA sequences are considered alternate polyadenylation signals. At the 5' end of the cDNA, the first ATG start codon is preceded by the sequence GCAGC, which is frequently associated with AGT start codons. The noncoding 5' region contains 60 nucleotides.

Example 17

Homology of 46 Kdalton Polypeptide and Murine Milk Fat Globule Antigen MFGE8

The BA46 cDNA sequence has considerable homology with the cDNA of a mouse milk fat globule glycoprotein MFGE8 of 66/55 Kdalton described by Stubbs et al, supra. The nucleotide sequence of the BA46 open reading frame has 76% identity with that of MFGE8. The 5' and 3' non-coding regions have 71% and 62% identities, respectively. The greatest % identity is present in the nucleotide sequences encoding the function domains, within the open reading frame, that are shared by the two encoded proteins as shown in Table 5 below.

TABLE 5

Homologies between 46 Kdalton HMFG Antigen
Polypeptide and MMFG Antigen Polypeptide (MFGE8)hz,1/51

| | | |
|---|---|---|
| 46KORF* | - MPRPRLLAALCGALLCAPSLLVALD-------------------------- | -25 |
| MFGE8PRO+ | - MQVSRVLLALCGMLLCASGLFAASGDFCDSSLCLNGGTCLTGQDNDIYCLCPEGF-like | -55 |
| 46KORF | - -----------------ICSKNPCHNGGLCEEISQEVRGDVFPSYTCTCLKGYAGNMCET- | -68 |
| MFGE8PRO | - TGLVCNETERGPCSPNPCYNDAKCLVTLDTQRGDIPTEYICQCPVGYSGIHCETE | -110 |
| 46KORF | - ----------------------------------------KCVEPLGHENGNZAHSQIA | -87 |
| MFGE8PRO | - TNYYNLDGEYMFTTAVPMTAVPTPAPTPDLSNNLASRCSTQLGMEGGAIADSQIS | -165 |
| 46KORF | - ASSVRVTFLGLQHWVPELARLNRAGMVNAWTPSSNDDNPWIQVNLLRRMWVTGW | -142 |
| MFGE8PRO | - ASYVYMGFMGLQRWGPELARLYRTGMVNANHASNYDSLPWIQVNLLRKMRVSGVM | -220 |
| 46KORF | - TQGASRLASHEYLKAFKVAYSLNGHEFDFINDVNKKMKEFVGNWKAVNNNLFE | -197 |
| MFGE8PRO | - TQGASRAGRAEYLKTFKVAYSLDGRKFEFIQDESGGDKEFLGNLDNHSLKVNMFN | -275 |
| 46KORF | - TPVEAQYVRLYPTSCHTACTLRFELLGCELNGCANPLGLKNNSXPDKQITASSSY | -252 |
| MFGE8PRO | - PTLEAEYIRLYPVSCHRGCTLRFELLGCELHGCLEPLGLKNKTIPDSQMSASSSY | -330 |
| 46KORF | - KTWGLHLFSWNPSYARLDKQGNFNAWVAGSYGNDQWLQVDLGSSKEVTGIITQGA | -307 |
| MFGE8PRO | - KTWNLRAFGWYPHLGRLDNQGKrNAWTAQSHSAKEWLQVDLGTQRQVTGIITQGA | -385 |
| 46KORF | - RNFGSVQFVASYKVAYSNDSANWREYQDPRTGSSKIFPGNWDHMSHODFETFI | -362 |
| MFGE8PRO | - RDFGHIQYVESYKVAHSDDGVQWTVYSEQ--GSSKVFQGNLDNNSHKKNIFEKPF | -438 |
| 46KORF | - LARYVRILPVAWNNRIALRLELLGC | -387 |
| MFGE8PRO | - MAAAVRVLPVSWHNRITLRLELLGC | -463 |

*(SEQ. ID No: 8)
+(SEQ. ID No: 9)
. Similar Amino Acid
: Identical Amino Acid

Example 18
Epitope Mapping

Overlapping peptide hexamers spanning amino acids 330–382 of the 46 Daltons HMFG polypeptide (BA46) sequence were synthesized onto the ends of polyethylene pins using an Epitope Scanning Kit (Cambridge Research Biochemicals, Cambridge, UK) as described by Geysen et al. (Geysen, et al. "Use of a peptide synthesis to probe vital antigens for epitopes to a resolution of a single amino acid", PNAS (USA) 81:3998–4002 (1984)). The polyethylene pins are arranged in a 8×12 configuration that fit into a 96 well microtiter dish and were supplied with a β-alanine attached to the ends to which the amino acids are added, consecutively using pentafluorophenyl active esters of fluorenylmethyloxycarbonyl(Fmoc)-L-amino acids. Each consecutive overlapping hexamer or octamer differed from the previous one by a single amino acid and were synthesized to span amino acids 330–382 of the BA46 peptide so that every combination of hexamer or octamer was present. The binding of monoclonal antibodies Mc3, Mc8, Mc15, Mc16 raised against the BA46 antigen as described by Peterson et al (Peterson et al., "Biochemical and histological characterization of antigens preferentially expressed on the surface and cytoplasm of breast carcinoma cells identified by monoclonal antibodies against the human milk fat globule", Hybridoma 9:221–235 (1990)) to the synthetic peptides was tested using the ELISA method with horse radish peroxidase-conjugated goat anti-mouse IgG (Promega, Madison, Wis.), and color development with 2,2' azinobis(3-ethylbenzothiazdine-6-sulfuric acid (Sigma, St. Louis, Mo.).

Example 19
Open Reading Frame and Antibody Binding Characteristics

The largest open reading frame of the BA46 cDNA encodes a protein of 387 amino acids with an estimated molecular weight of 43,123 Daltons. The actual correspondence of the cDNA cloned to the BA46 glycoprotein antigen isolated from the HMFG was shown by the correlation of the BA46 mRNA with the expression to the BA46 antigen in different breast cell lines (Larocca et al., "A 46 Kdalton human milk fat globule glycoprotein that is highly expressed in carcinoma cells has homology with human clotting factors V and VIII", Cancer Res. 51: 994 (1991)) and the binding of the monoclonal antibodies used to in the cDNA screening to the pEX/LB21 fusion protein expressed in E. coli (Larocca et al., "Molecular cloning and expression of breast mucin-associated antigens", in Breast Epithelial Antigens: Molecular Biology to Clinical Applications, R. L. Ceriani, Ed., pp. 35–44, New York Plenum Press (1991)). In addition, 5 defined and distinct amino acid sequence epitopes in the C-terminal end of the protein were determined by epitope mapping for two monoclonal antibodies of the cocktail used in the original screening of the cDNA library (Mc8=DPRTG; and Mc16=SSKIF) (See, Table 4 above). The two other monoclonal antibodies (Mc3, Mc15) neither bind to the pEX/LB21 fusion protein nor to any of the peptide hexamers used in the epitope mapping of the C-terminal region (amino acids 330–382) of the 46 Kdalton polypeptide.

Example 20
Homology of 46 Kdalton Polypeptide (BA46) with Other Known Proteins

The amino acid sequence deduced with the help of the PC/GENE DNA and the protein analysis program (IntelliGenetics, Inc.) revealed the existence of homologies with several functional domains. At the N-terminal end, there is a hydrophobic region after the Met start codon which most likely corresponds to a signal peptide. Cleavage most likely occurs between the $val_{21}$ and $ala_{22}$, leaving a cleaved peptide of 21 amino acids plus the methionine. This cleavage results in a processed polypeptide of 40,862 Kdalton s. Amino acids 46 to 48 represent a known cell adhesion sequence (RGD), and following this is an EGF-like domain (amino acids 55 to 66). The C-terminal end, starting at amino acid 69 comprises a domain with homology to the C1/C2 region of human coagulation factors V and VIII, a portion of which is shown in Table 1 above. The sequence contains four potential N-linked glycosylation sites, all present in the C1C2-like domain, numerous potential O-linked glycosylation sites, disulfide linkages, and phosphorylation sites (protein kinase C and casein kinase II). The greatest homology to other proteins is seen with the 66/55 Kdalton antigen MFGE8 isolated from mouse milk fat globule (Stubbs et al., supra) as shown in Table 5 above and Table 6 below.

the same cell adhesion purpose. Viruses whose surface proteins contain the RGD sequence include the coxsackie virus, the foot-and-mouth disease virus, the human immunodeficiency virus type 1 (HIV1), and certain flaviviruses such as Murray Valley encephalitis virus, the Japanese encephalitis virus, the yellow fever virus, the West Nile virus Dengue type 4 virus, and the tick-borne encephalitis virus. The interaction of the cell adhesion sequence with its cell receptor is inhibited by synthetic peptides containing the RGD peptide.

The function of the EGF-like sequences is not known. However, this sequence is present on a number of growth factors, proteins associated with cell interaction and adhesion, and developmental proteins. The growth factors include TGF-alpha, amphiregulin, and growth factor-related

TABLE 6

Comparison of Deduced 46 Kdalton HMFG Antigen Sequence to other Protein Sequences

| BA46C1: | Human 46 Kdalton Milk Fat Globule Polypeptide | | | (Clone 1) |
|---|---|---|---|---|
| BA46C2: | " | | | (Clone 2) |
| MFGE8C1: | Murine Milk Fat Globule Antigen Polypeptide | | | (Clone 1) |
| MFGE8C2: | " | | | (Clone 2) |
| FA5C1: | Coagulauon | Factor | V | (Clone 1) |
| FA5C2: | " | " | V | (Clone 2) |
| FA8C1: | " | " | VIII | (Clone 1) |
| FA8C2: | " | " | VIII | (Clone 2) |
| A5C1: | A5 | | Protein | (Clone 1) |
| A5C2: | A5 | | Protein | (Clone 2) |
| DDRC1: | DDR | | Protein | (Clone 1) |
| DISC: | Discoidin | | Protein | |
| GPSS: | | | Protein | |
| BAND16: | | | Protein | |

The difference between the human 46 Kdalton polypeptide (BA46) and MFG-E8 is that the former has a single EGF-like sequence and lacks the proline rich region that is present between the second EGF-like sequence and the C1C2-like sequence of coagulation factors V and VIII in MFG-E8 (See, Table 6 above). The cell adhesion sequence RDG is also present in MFG-E8 but was not noted by the authors when published (Stubbs et al., supra), which is separated by the EGF-like sequence in both mouse and human proteins by 6 amino acids (See, Table 6 above). All cysteines in the human 46 Kdalton polypeptide are in identical positions compared to MFG-E8, two in the signal peptide, 3 preceding the RGD sequence, 3 in the EGF-like sequences, and 5 in the C1/C2-like sequence. Both proteins have 4 N-linked glycosylation sites, but in the human 46 Kdalton polypeptide all are present in the C1C2-like sequence, while in MFG-E8, three are in the C1C2-like sequence and one after the first EGF-like sequence that is absent from the 46 Kdalton polypeptide. The second N-linked glycosylation site on the human 46 Kdalton polypeptide occurs is in the same position as in MFG-E8.

The cell adhesion sequence (RGD) was originally found in fibronectin and shown to be crucial for interaction with its cell surface receptor, such as the integrins (Cherny et al, J. Biol. Chem. 268:9725 (1993)). Other proteins containing this cell adhesion sequence (RGD) are fibrinogen, vitronectin, Von Willebrand coagulation factor, entactin, some isoforms of tumor growth factor beta, and slime mold discoidin I (Poole et al., "Sequence and expression of the discoudin I gene family in dictyostelium", J. Mol. Biol. 153:273–289 (1981)).

The RGD sequence is also found on some collagens and on surface proteins of some animal viral proteins that serve proteins of the vaccinia, myxoma, and shope fibroma viruses. The EGF-like sequence is also present on coagulation associated proteins, complement components, fbronectin, selecting, and several Drosophila developmental proteins such as the Notch-1, the neurogenic repetitive locus proteins, 95F and delta).

The C1C2 domain of human coagulation factors V and VIII has been shown to be involved in phospholipid binding, that is an essential property for the involvement of these factors in coagulation. The binding appears to be to phosphatidylserine (Ortel et al., "Deletion analysis of recombinant human factor V. Evidence for a phosphotidylserine binding site in the second C-type domain", J. Biol. Chem. 267:4189–4198 (1992)). The 46 Kdalton polypeptide appears to be a member of a family of proteins that contain these C-type domains (See, Table 6). These include the mouse milk fat globule protein MFG-E8 (Stubbs et al., supra), a putative neuronal cell adhesion molecule (A5 antigen) of Xenopus laevis (Takagi et al., "The A5 Antigen, a candidate for the neuronal recognition molecule, has homologies to complement components and coagulation factors", Neuron 7: 295–307 (1991)), a receptor tyrosine kinase found in human breast carcinoma (DDR), and discoidin I, an endogenous lectin of slime mold Dictyostellum discoideum (Poole et al., supra). The coagulation factors, BA46, MFG-E8, and the A5 antigen have two C-type domains that apparently resulted from an earlier tandem duplication. Both DDR and discoidin I have single C-type domains and appear to be primitive members of the family.

Example 21
Dendrogram of Protein Family

Figure 2:
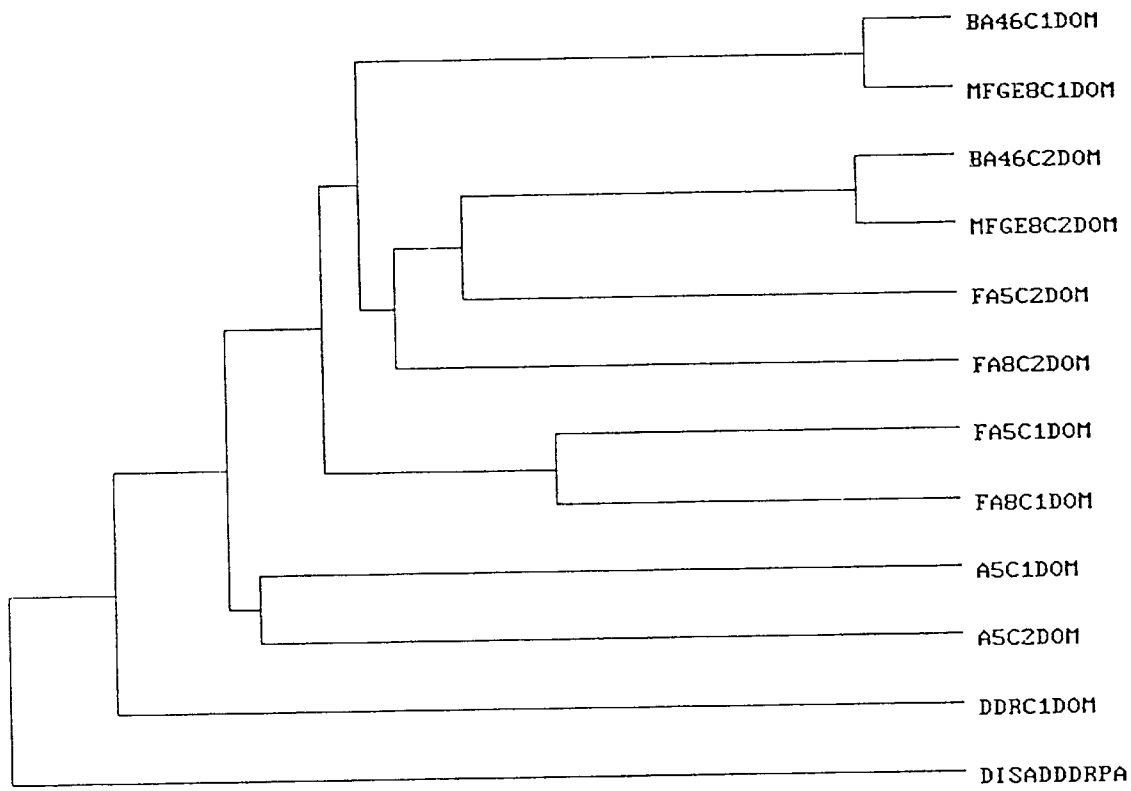
FIG. 2 shows a dendrogram of the aligned C-type domains for various related proteins.

A dendrogram of the alignment of the C-type domains shown in Table 6 above was constructed and shows that this alignment likely occurred and split human protein DDR and slime mold discoidin I from the other proteins with C1 and C2 domains. The dendrogram is shown in FIG. 2 accompanying this patent.

A separation of the Xenopus A5 antigen from the other human coagulation factors and the mouse and human milk fat globule proteins appears to have occurred thereafter. Finally, the coagulation factors were later separated from the milk fat globule proteins. The C1C2 domain appears to have evolved as a unit, since the C1 regions of BA46 and MFG-E8 have more homology than with their own C2 domains. This is also the case for the C1 and C2 domains of factors V and VIII (See, Table 6 above). In fact, the C2 domains of the coagulation factors are more homologous to the BA46 and MFG-E8 C2 domains than they are to the their own C1 domains. The similarity also extends to the sequences of the peptides from the milk fat globule components of bovine (component 16) and guinea-pig (GP-55) (Mather et al., "The major fat-globule membrane proteins, bovine components 15/16 and guinea-pig GP 55, are homologous to MGF-E8, a murine glycoprotein containing epidermal growth factor-like and factor V/VIII-like sequences", Biochem. Mol. Biol. Int. 29: 545–554, 1993)). (See, Table 6 above).

The C2 domain of the coagulation factors is critical for phospholipid binding. This is also most likely the case for the C2-like domains of the milk fat globule factors, including the 46 Kdalton HMFG polypeptide of the invention. The current evidence suggests that the MFG-E8 antigen binds to phospholipids, and that this binding is $Ca^{++}$ dependent (Buse et al, J. Cell Biol. 115:1969 (1991)). In contrast, the replacement of the C2 domain of factor V with the C2-like domain of the 46 Kdalton HMFG polypeptide was shown to abolish the phospholipid binding properties in the chimeric protein, while its replacement with the C2 domain of factor VIII did not (Ortel et al., "Epitope mapping of the C2 domain of coagulation factor V using antibodies and chimeras with heterologous C-type domains" (1993)). In contrast to the phospholipid binding reported by Parry et al, supra, this binding is not $Ca^{++}$ dependent.

These results permit the grouping of the 46 Kdalton HMFG polypeptide with growth factors and other molecules associated with cell adhesioninteractions, e.g. associated with breast epithelial cells, that provide a possible autocrine/paracrine function. The 46 Kdalton HMFG antigen is thus related to selectin-like molecules (Larigan, J. D., Tsang, T. C., Rumberger, J. M., and Burns, D. K., "Characterization of cDNA and genomic sequences encoding rabbit ELAM-1: Conservation of structure and functional interactions with leukocytes", DNA Cell Biol. 11:149–162 (1992)), which have the general structure of an N-terminal adhesion domain (lectin domain) followed by an EGF-like domain, a variable number of complement regulatory elements, a membrane attachment domain (a single transmembrane sequence) and a short cytoplasmic tail (Larigan, J. D., Tsang, T. C., Rumberger, J. M., and Burns, D. K., "Characterization of cDNA and genomic sequences encoding rabbit ELAM-1: conservation of structure and functional interactions with leukocytes", DNA Cell Biol. 11:149–162 (1992)). The C-type domain is very likely the means by which the 46 Kdalton HMFG polypeptide associates with the cell membrane by interaction with phospholipids. The possible cell adhesion properties may be mediated via the cell adhesion sequence RGD since breast cells are known to possess integrins that have receptors for this sequence. The autocrine may be mediated by the EGF-like sequence. The 46 Kdalton HMFG antigen is abundantly present in the HMFG and the expression of its mouse homologue is increased during lactation (Stubbs et al., supra). Thus, the expression of the human 46 Kdalton HMFG antigen and its mouse homologue appear to be associated with differentiation in the breast.

The overexpression of the 46 Kdalton antigen mRNA in some breast, lung and ovarian cancers such as carcinomas shows that the 46 Kdalton antigen is expressed with other epithelial tissues and may be deregulated in malignancy. Its expression in breast cancers such as carcinomas makes it a good target for monoclonal antibody therapy. Of the known monoclonal antibodies raised against the 46 Kdalton HMFG antigen, Mc3, which recognizes an epitope in the N-terminal region of the polypeptide, is more effective in radioimmunotherapy than Mc8, which recognizes an epitope in the C2-like domain of the 46 Kdalton polypeptide (unpublished results). This effectiveness of Mc3 in radioimmunotherapy is in all likelyhood the result of an internalization of the antigen-antibody complex formed, which increases the residence time of the radiolabel in the tumor. In addition, the antibody is likely involved in modulating cell growth by interfering with the effect of the target antigen on growth regulation and cell association.

The anti-viral activity of the 46 Kdalton HMFG polypeptide appears to be mediated via binding of the antigen to the virus (Yolken et al., "Human milk mucin inhibits rotavirus replication and prevents experimental gastroenteritis", J. Clin. Invest. 90: 1984–1991 (1992)). The desialylation of the 46 Kdalton HMFG polypeptide was shown to abolish its anti-viral activity (Yolken et al., supra.)

Example 22

Bacterial Expression of Complete 46 Kdalton HMFG Antigen

A recombinant polynucleotide and its polypeptide product encompassing the entire 46 Kdalton HMFG antigen were produced by cloning the BA46 cDNA segment that codes for entire ORF except for the signal peptide obtained above. Poly A containing mRNA was isolated from a breast cell line (ELL-G) using the FastTrack mRNA isolation kit (Invitrogen, San Diego) according to the manufacturer's instructions. The mRNA was reversed transcribed and amplified using an upstream primer at the 3' end of the signal peptide encoding sequence and a downstream primer at the first stop codon. Each primer was constructed to have a HindIII restriction enzyme site. The amplified sequence was then cut with the restriction enzymes StuI and ApaI, which cut it into three fragments. These fragments were cloned into a pBS vector and sequenced to verified that no mutations were introduced by the PCR reactions. Once the identity of the sequence fragments was verified, the fragments were ligated together and cloned into the pBR322/lacP/OmpA and pBS//OmpA expression vectors. The expression of the product in the vector was thus driven by the LacP promoter and and a bacterial signal peptide substituted for the BA46 signal peptide. Both vectors, when transfected into E. coli, expressed the 46 Kdalton HMFG antigen. The presence of the product was observed in the medium, periplasm, and protoplast of the transfected E. coli. The authenticity and identity of the recombinant peptide produced was demonstrated by binding of all available anti-46 Kdalton HMFG antigen monoclonal antibodies, Mc3, Mc8, Mc15, Mc16, to the transfected E. coli extracts in a solid phase radioimmunobinding assay. All the monoclonal antibodies recognized epitopes on the peptide core of the 46 Kdalton HMFG antigen. No monoclonal antibody bound to control bacteria extracts transfected with the same vectors but without the insert.

What is claimed as novel and unobvious in Letters Patent of the United States is:

1. A purified, isolated polypeptide consisting of
an amino acid sequence encoded by a nucleic acid consisting of a sequence selected from the group consisting of nucleotides 1–1221 of SEQ. ID No: 7 and nucleotides 1–654 of SEQ. ID No: 1;
hexapeptides comprising six contiguous amino acid residues from 332 to 382 of SEQ. ID NO:6; and
an amino acid sequence encoded by nucleotides 64–1221 of SEQ. ID No: 7 in non-denatured form.

2. The polypeptide of claim 1, consisting of the amino acid sequence encoded by nucleotides 64–1221 of SEQ. ID No: 7 in non-denatured form.

3. The polypeptide of claim 1, consisting of an amino acid sequence selected from the group consisting of the amino acid sequence encoded by nucleotides 1–654 of SEQ. ID No: 1 and the amino acid sequence encoded by nucleotides 1–1221 of SEQ. ID NO:7.

4. The polypeptide of claim 1, consisting of the amino acid sequence encoded by nucleotides 1–1221 of SEQ. ID NO:7.

5. The polypeptide of claim 1, in glycosylated form.

6. The polypeptide of claim 1, in unglycosylated form.

7. The polypeptide of claim 1, consisting of an amino acid sequence selected from the group consisting of amino acids 22–387 of SEQ. ID No: 6, SEQ. ID No: 2, SEQ. ID No: 3, and SEQ. ID NO:6 in non-denatured form.

8. The polypeptide of claim 7, consisting of SEQ. ID No: 6 in non-denatured form.

9. The polypeptide of claim 7, consisting of amino acids 22–387 of SEQ. ID No: 6.

10. The polypeptide of claim 7, consisting of SEQ. ID No: 2.

11. The polypeptide of claim 7, consisting of SEQ. ID No: 3.

12. A composition, comprising the polypeptide of claim 1, and a non-proteolytic carrier.

13. The composition of claim 12, wherein the non-proteolytic carrier comprises a biologically acceptable carrier.

14. The composition of claim 13, wherein the biologically acceptable carrier comprises a pharmaceutically acceptable carrier.

15. A fusion protein, comprising an amino acid sequence of the polypeptide of claim 1 linked to a peptide unrelated to the HMFG differentiation antigen.

16. The fusion protein of claim 15, wherein the peptide is about 10 to 1,000 amino acids long.

17. The fusion protein of claim 15, in unglycosylated form.

18. The fusion protein of claim 15, in unglycosylated form.

19. A composition, comprising the fusion protein of claim 15, and a non proteolytic carrier.

20. The composition of claim 19, wherein the carrier comprises a biologically acceptable carrier.

21. The composition of claim 19, wherein the carrier comprises a pharmaceutically acceptable carrier.

22. The polypeptide of claim 1, consisting of a hexapeptide comprising six contiguous amino acid residues from 332 to 382 of SEQ. ID NO:6.

* * * * *

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
       (A) LENGTH: 1384 base pairs
       (B) TYPE: nucleic acid
       (C) STRANDEDNESS: both
       (D) TOPOLOGY: linear (ii) MOLECULE TYPE: cDNA (xi) SEQUENCE DESCRIPTION: SEQ ID NO:1:

| | | | | | |
|---|---|---|---|---|---|
| GATTTCATCC | ATGATGTTAA | TAAAAAACAC | AAGGAGTTTG | TGGGTAACTG | GAACAAAAAC | 60 |
| GCGGTGCATG | TCAACCTGTT | TGAGACCCCT | GTGGAGGCTC | AGTACGTGAG | ATTGTACCCC | 120 |
| ACGAGCTGCC | ACACGGCCTG | CACTCTGCGC | TTTGAGCTAC | TGGGCTGTGA | GCTGAACGGA | 180 |
| TGCGCCAATC | CCCTGGGCCT | GAAGAATAAC | AGCATCCCTG | ACAAGCAGAT | CACGGCCTCC | 240 |
| AGCAGCTACA | AGACCTGGGG | CTTGCATCTC | TTCAGCTGGA | ACCCCTCCTA | TGCACGGCTG | 300 |
| GACAAGCAGG | GCAACTTCAA | CGCCTGGGTT | GCGGGGAGCT | ACGGTAACGA | TCAGTGGCTG | 360 |
| CAGGTGGACC | TGGGCTCCTC | GAAGGAGGTG | ACAGGCATCA | TCACCCAGGG | GGCCCGTAAC | 420 |
| TTTGGCTCTG | TCCAGTTTGT | GGCATCCTAC | AAGGTTGCCT | ACAGTAATGA | CAGTGCGAAC | 480 |
| TGGACTGAGT | ACCAGGACCC | CAGGACTGGC | AGCAGTAAGA | TCTTCCCTGG | CAACTGGGAC | 540 |
| AACCACTCCC | ACAAGAAGAA | CTTGTTTGAG | ACGCCCATCC | TGGCTCGCTA | TGTGCGCATC | 600 |
| CTGCCTGTAG | CCTGGCACAA | CCGCATCGCC | CTGCGCCTGG | AGCTGCTGGG | CTGTTAGTGG | 660 |
| CCACCTGCCA | CCCCCAGGTC | TTCCTGCTTT | CCATGGGCCC | GCTGCCTCTT | GGCTTCTCAG | 720 |
| CCCCTTTAAA | TCACCATAGG | GCTGGGGACT | GGGGAAGGGG | AGGGTGTTCA | GAGGCAGCAC | 780 |
| CACCACACAG | TCACCCCTCC | CTCCCTCTTT | CCCACCCTCC | ACCTCTCACG | GGCCCTGCCC | 840 |
| CAGCCCCTAA | GCCCCGTCCC | CTAACCCCCA | GTCCTCACTG | TCCTGTTTTC | TTAGGCACTG | 900 |
| AGGGATCTGA | GTAGGTCTGG | GATGGACAGG | AAAGGGCAAA | GTAGGGCGTG | TGGTTTCCCT | 960 |
| GCCCCTGTCC | GGACCGCCGA | TCCCAGGTGC | GTGTGTCTCT | GTCTCTCCTA | GCCCCTCTCT | 1020 |
| CACACATCAC | ATTCCCATGG | TGGCCTCAAG | AAAGGCCCGG | AAGCCCCAGG | CTGGAGATAA | 1080 |
| CAGCCTCTTG | CCCGTCGGCC | CTGCGTCGGC | CCTGGGGTAC | CATGTGCCAC | AACTGCTGTG | 1140 |
| GCCCCTGTC | CCCAAGACAC | TTCCCCTTGT | CTCCCTGGTT | GCCTCTCTTG | CCCCTTGTCC | 1200 |
| TGAAGCCCAG | CGACACAGAA | GGGGGTGGGG | CGGGTCTATG | GGGAGAAAGG | GAGCGAGGTC | 1260 |
| AGAGGAGGGC | ATGGGTTGGC | AGGGTGGGCG | TTTGGGCCC | TCATGCTGGC | TTTTCACCCC | 1320 |
| AGAGGACACA | GGCAGCTTCC | AAAATATATT | TATCTTCTTC | ACGGGAAAAA | AAAAAAAAAA | 1380 |
| ACCG | | | | | | 1384 |

(2) INFORMATION FOR SEQ ID NO:2:

(i) SEQUENCE CHARACTERISTICS:
       (A) LENGTH: 218 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:2:

Asp Phe Ile His Asp Val Asn Lys Lys His Lys Glu Phe Val Gly Asn
1               5                   10                  15

Trp Asn Lys Asn Ala Val His Val Asn Leu Phe Glu Thr Pro Val Glu
                20                  25                  30

Ala Gln Tyr Val Arg Leu Tyr Pro Thr Ser Cys His Thr Ala Cys Thr
            35                  40                  45

Leu Arg Phe Glu Leu Leu Gly Cys Glu Leu Asn Gly Cys Ala Asn Pro
    50                  55                  60

Leu Gly Leu Lys Asn Asn Ser Ile Pro Asp Lys Gln Ile Thr Ala Ser
65                  70                  75                  80

Ser Ser Tyr Lys Thr Trp Gly Leu His Leu Phe Ser Trp Asn Pro Ser
                85                  90                  95

Tyr Ala Arg Leu Asp Lys Gln Gly Asn Phe Asn Ala Trp Val Ala Gly
            100                 105                 110

Ser Tyr Gly Asn Asp Gln Trp Leu Gln Val Asp Leu Gly Ser Ser Lys
        115                 120                 125

Glu Val Thr Gly Ile Ile Thr Gln Gly Ala Arg Asn Phe Gly Ser Val
130                 135                 140

Gln Phe Val Ala Ser Tyr Lys Val Ala Tyr Ser Asn Asp Ser Ala Asn
145                 150                 155                 160

Trp Thr Glu Tyr Gln Asp Pro Arg Thr Gly Ser Ser Lys Ile Phe Pro
                165                 170                 175

Gly Asn Trp Asp Asn His Ser His Lys Lys Asn Leu Phe Glu Thr Pro
            180                 185                 190

Ile Leu Ala Arg Tyr Val Arg Ile Leu Pro Val Ala Trp His Asn Arg
        195                 200                 205

Ile Ala Leu Arg Leu Glu Leu Leu Gly Cys
    210                 215

(2) INFORMATION FOR SEQ ID NO:3:

(i) SEQUENCE CHARACTERISTICS:
        (A) LENGTH: 217 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:3:

Phe Ile His Asp Val Asn Lys Lys His Lys Glu Phe Val Gly Asn Trp
1               5                   10                  15

Asn Lys Asn Ala Val His Val Asn Leu Phe Glu Thr Pro Val Glu Ala
                20                  25                  30

Gln Tyr Val Arg Leu Tyr Pro Thr Ser Cys His Thr Ala Cys Thr Leu
            35                  40                  45

Arg Phe Glu Leu Leu Gly Cys Glu Leu Asn Gly Cys Ala Asn Pro Leu
    50                  55                  60

Gly Leu Lys Asn Asn Ser Ile Pro Asp Lys Gln Ile Thr Ala Ser Ser
65                  70                  75                  80

Ser Tyr Lys Thr Trp Gly Leu His Leu Phe Ser Trp Asn Pro Ser Tyr
                85                  90                  95

Ala Arg Leu Asp Lys Gln Gly Asn Phe Asn Ala Trp Val Ala Gly Ser
            100                 105                 110

```
Tyr Gly Asn Asp Gln Trp Leu Gln Val Asp Leu Gly Ser Ser Lys Glu
            115                 120                 125

Val Thr Gly Ile Ile Thr Gln Gly Ala Arg Asn Phe Gly Ser Val Gln
130                 135                 140

Phe Val Ala Ser Tyr Lys Val Ala Tyr Ser Asn Asp Ser Ala Asn Trp
145                 150                 155                 160

Thr Glu Tyr Gln Asp Pro Arg Thr Gly Ser Ser Lys Ile Phe Pro Gly
            165                 170                 175

Asn Trp Asp Asn His Ser His Lys Lys Asn Leu Phe Glu Thr Pro Ile
            180                 185                 190

Leu Ala Arg Tyr Val Arg Ile Leu Pro Val Ala Trp His Asn Arg Ile
            195                 200                 205

Ala Leu Arg Leu Glu Leu Leu Gly Cys
210                 215
```

(2) INFORMATION FOR SEQ ID NO:4:

(i) SEQUENCE CHARACTERISTICS:
        (A) LENGTH: 218 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:4:

```
Phe Lys Gly Asn Ser Thr Arg Asn Val Met Tyr Phe Asn Gly Asn Ser
1                   5                   10                  15

Asp Ala Ser Thr Ile Lys Glu Asn Gln Phe Asp Pro Pro Ile Val Ala
            20                  25                  30

Arg Tyr Ile Arg Ile Ser Pro Thr Arg Ala Tyr Asn Arg Pro Thr Leu
            35                  40                  45

Arg Leu Glu Leu Gln Gly Cys Glu Val Asn Gly Cys Ser Thr Pro Leu
50                  55                  60

Gly Met Glu Asn Gly Lys Ile Glu Asn Lys Gln Ile Thr Ala Ser Ser
65                  70                  75                  80

Phe Lys Lys Ser Trp Trp Gly Asp Tyr Trp Glu Pro Phe Arg Ala Arg
            85                  90                  95

Leu Asn Ala Gln Gly Arg Val Asn Ala Trp Gln Ala Lys Ala Asn Asn
            100                 105                 110

Asn Lys Gln Trp Leu Glu Ile Asp Leu Leu Lys Ile Lys Lys Ile Thr
            115                 120                 125

Ala Ile Ile Thr Gln Gly Cys Lys Ser Leu Ser Ser Glu Met Tyr Val
            130                 135                 140

Lys Ser Tyr Thr Ile His Tyr Ser Glu Gln Gly Val Glu Trp Lys Pro
145                 150                 155                 160

Tyr Arg Leu Lys Ser Ser Met Val Asp Lys Ile Phe Glu Gly Asn Thr
            165                 170                 175

Asn Thr Lys Gly His Val Lys Asn Phe Phe Asn Pro Pro Ile Ile Ser
            180                 185                 190

Arg Phe Ile Arg Val Ile Pro Lys Thr Trp Asn Gln Ser Ile Ala Leu
            195                 200                 205

Arg Leu Glu Leu Phe Gly Cys Asp Ile Tyr
            210                 215
```

(2) INFORMATION FOR SEQ ID NO:5:

(i) SEQUENCE CHARACTERISTICS:

(A) LENGTH: 218 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:5:

Tyr Arg Gly Asn Ser Thr Gly Thr Leu Met Val Phe Phe Gly Asn Val
 1               5                  10                  15

Asp Ser Ser Gly Ile Lys His Asn Ile Phe Asn Pro Pro Ile Ile Ala
                20                  25                  30

Arg Tyr Ile Arg Leu His Pro Thr His Tyr Ser Ile Arg Ser Thr Leu
            35                  40                  45

Arg Met Glu Leu Met Gly Cys Asp Leu Asn Ser Cys Ser Met Pro Leu
50                  55                  60

Gly Met Glu Ser Lys Ala Ile Ser Asp Ala Gln Ile Thr Ala Ser Ser
65                  70                  75                  80

Tyr Phe Thr Asn Met Phe Ala Thr Trp Ser Pro Ser Lys Ala Arg Leu
                85                  90                  95

His Leu Gln Gly Arg Ser Asn Ala Trp Arg Pro Gln Val Asn Asn Pro
            100                 105                 110

Lys Glu Trp Leu Gln Val Asp Phe Gln Lys Thr Met Lys Val Thr Gly
        115                 120                 125

Val Thr Thr Gln Gly Val Lys Ser Leu Leu Thr Glu Met Tyr Val Lys
    130                 135                 140

Glu Phe Leu Ile Ser Ser Ser Gln Asp Gly His Gln Trp Thr Leu Phe
145                 150                 155                 160

Phe Gln Asn Gly Lys Val Lys Val Phe Gln Gly Asn Gln Asp Ser Phe
                165                 170                 175

Thr Pro Val Val Asn Ser Leu Asp Pro Pro Leu Leu Thr Arg Tyr Leu
            180                 185                 190

Arg Ile His Pro Gln Ser Trp Val His Gln Ile Ala Leu Arg Met Glu
        195                 200                 205

Val Leu Gly Cys Glu Ala Gln Asp Leu Tyr
    210                 215

(2) INFORMATION FOR SEQ ID NO:6:

(i) SEQUENCE CHARACTERISTICS:
        (A) LENGTH: 387 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:6:

Met Pro Arg Pro Arg Leu Leu Ala Ala Leu Cys Gly Ala Leu Leu Cys
 1               5                  10                  15

Ala Pro Ser Leu Leu Val Ala Leu Asp Ile Cys Ser Lys Asn Pro Cys
                20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
50                  55                  60

His Cys Glu Thr Lys Cys Val Glu Pro Leu Gly Met Glu Asn Gly Asn
65                  70                  75                  80

```
Ile Ala Asn Ser Gln Ile Ala Ala Ser Ser Val Arg Val Thr Phe Leu
                85                  90                  95
Gly Leu Gln His Trp Val Pro Glu Leu Ala Arg Leu Asn Arg Ala Gly
            100                 105                 110
Met Val Asn Ala Trp Thr Pro Ser Asn Asp Asp Asn Pro Trp Ile
            115                 120                 125
Gln Val Asn Leu Leu Arg Arg Met Trp Val Thr Gly Val Val Thr Gln
        130                 135                 140
Gly Ala Ser Arg Leu Ala Ser His Glu Tyr Leu Lys Ala Phe Lys Val
145                 150                 155                 160
Ala Tyr Ser Leu Asn Gly His Glu Phe Asp Phe Ile His Asp Val Asn
                165                 170                 175
Lys Lys His Lys Glu Phe Val Gly Asn Trp Asn Lys Asn Ala Val His
            180                 185                 190
Val Asn Leu Phe Glu Thr Pro Val Glu Ala Gln Tyr Val Arg Leu Tyr
            195                 200                 205
Pro Thr Ser Cys His Thr Ala Cys Thr Leu Arg Phe Glu Leu Leu Gly
        210                 215                 220
Cys Glu Leu Asn Gly Cys Ala Asn Pro Leu Gly Leu Lys Asn Asn Ser
225                 230                 235                 240
Ile Pro Asp Lys Gln Ile Thr Ala Ser Ser Tyr Lys Thr Trp Gly
                245                 250                 255
Leu His Leu Phe Ser Trp Asn Pro Ser Tyr Ala Arg Leu Asp Lys Gln
            260                 265                 270
Gly Asn Phe Asn Ala Trp Val Ala Gly Ser Tyr Gly Asn Asp Gln Trp
            275                 280                 285
Leu Gln Val Asp Leu Gly Ser Ser Lys Glu Val Thr Gly Ile Ile Thr
        290                 295                 300
Gln Gly Ala Arg Asn Phe Gly Ser Val Gln Phe Val Ala Ser Tyr Lys
305                 310                 315                 320
Val Ala Tyr Ser Asn Asp Ser Ala Asn Trp Thr Glu Tyr Gln Asp Pro
                325                 330                 335
Arg Thr Gly Ser Ser Lys Ile Phe Pro Gly Asn Trp Asp Asn His Ser
            340                 345                 350
His Lys Lys Asn Leu Phe Glu Thr Pro Ile Leu Ala Arg Tyr Val Arg
        355                 360                 365
Ile Leu Pro Val Ala Trp His Asn Arg Ile Ala Leu Arg Leu Glu Leu
        370                 375                 380
Leu Gly Cys
385

(2) INFORMATION FOR SEQ ID NO:7:

(i) SEQUENCE CHARACTERISTICS:
        (A) LENGTH: 1934 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:7:

AGAACCCCGC GGGGTCTGAG CAGCCCAGCG TGCCCATTCC AGCGCCCGCG TCCCCGCAGC        60

ATGCCGCGCC CCGCCCTGCT GGCCGCGCTG TGCGGCGCGC TGCTCTGCGC CCCCAGCCTC       120

CTCGTCGCCC TGGATATCTG TTCCAAAAAC CCCTGCCACA ACGGTGGTTT ATGCGAGGAG       180
```

-continued

```
ATTTCCCAAG AAGTGCGAGG AGATGTCTTC CCCTCGTACA CCTGCACGTG CCTTAAGGGC      240

TACGCGGGCA ACCACTGTGA GACGAAATGT GTCGAGCCAC TGGGCATGGA GAATGGGAAC      300

ATTGCCAACT CACAGATCGC CGCCTCATCT GTGCGTGTGA CCTTCTTGGG TTTGCAGCAT      360

TGGGTCCCGG AGCTGGCCCG CCTGAACCGC GCAGGCATGG TCAATGCCTG GACACCCAGC      420

AGCAATGACG ATAACCCCTG GATCCAGGTG AACCTGCTGC GGAGGATGTG GGTAACAGGT      480

GTGGTGACGC AGGGTGCCAG CCGCTTGGCC AGTCATGAGT ACCTGAAGGC CTTCAAGGTG      540

GCCTACAGCC TTAATGGACA CGAATTCGAT TCATCCATG ATGTTAATAA AAAACACAAG       600

GAGTTTGTGG GTAACTGGAA CAAAAACGCG GTGCATGTCA ACCTGTTTGA GACCCCTGTG      660

GAGGCTCAGT ACGTGAGATT GTACCCCACG AGCTGCCACA CGGCCTGCAC TCTGCGCTTT      720

GAGCTACTGG GCTGTGAGCT GAACGGATGC GCCAATCCCC TGGGCCTGAA GAATAACAGC      780

ATCCCTGACA AGCAGATCAC GGCCTCCAGC AGCTACAAGA CCTGGGGCTT GCATCTCTTC      840

AGCTGGAACC CCTCCTATGC ACGGCTGGAC AAGCAGGGCA ACTTCAACGC CTGGGTTGCG      900

GGGAGCTACG GTAACGATCA GTGGCTGCAG GTGGACCTGG GCTCCTCGAA GGAGGTGACA      960

GGCATCATCA CCCAGGGGGC CCGTAACTTT GGCTCTGTCC AGTTTGTGGC ATCCTACAAG     1020

GTTGCCTACA GTAATGACAG TGCGAACTGG ACTGAGTACC AGGACCCCAG GACTGGCAGC     1080

AGTAAGATCT TCCCTGGCAA CTGGGACAAC CACTCCCACA GAAGAACTT GTTTGAGACG      1140

CCCATCCTGG CTCGCTATGT GCGCATCCTG CCTGTAGCCT GGCACAACCG CATCGCCCTG     1200

CGCCTGGAGC TGCTGGGCTG TTAGTGGCCA CCTGCCACCC CCAGGTCTTC CTGCTTTCCA     1260

TGGGCCCGCT GCCTCTTGGC TTCTCAGCCC CTTTAAATCA CCATAGGGCT GGGGACTGGG     1320

GAAGGGGAGG GTGTTCAGAG GCAGCACCAC CACACAGTCA CCCCTCCCTC CCTCTTTCCC     1380

ACCCTCCACC TCTCACGGGC CCTGCCCCAG CCCCTAAGCC CCGTCCCCTA ACCCCAGTC      1440

CTCACTGTCC TGTTTTCTTA GGCACTGAGG GATCTGAGTA GGTCTGGGAT GGACAGGAAA     1500

GGGCAAAGTA GGGCGTGTGG TTTCCCTGCC CCTGTCCGGA CCGCCGATCC CAGGTGCGTG     1560

TGTCTCTGTC TCTCCTAGCC CCTCTCTCAC ACATACATT CCCATGGTGG CCTCAAGAAA      1620

GGCCCGGAAG CCCCAGGCTG GAGATAACAG CCTCTTGCCC GTCGGCCCTG CGTCGGCCCT     1680

GGGGTACCAT GTGCCACAAC TGCTGTGGCC CCCTGTCCCC AAGACACTTC CCCTTGTCTC     1740

CCTGGTTGCC TCTCTTGCCC CTTGTCCTGA AGCCCAGCGA CACAGAAGGG GGTGGGGCGG     1800

GTCTATGGGG AGAAAGGGAG CGAGGTCAGA GGAGCCGGCA TGGGTTGGCA GGGTGGGCGT     1860

TTGGGGCCCT CATGCTGGCT TTTCACCCCA GGAGGACACAG GCAGCTTCCA AAATATATTT    1920

ATCTTCTTCA CGGG                                                       1934
```

(2) INFORMATION FOR SEQ ID NO:8:

(i) SEQUENCE CHARACTERISTICS:
        (A) LENGTH: 465 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:8:

```
Met Pro Arg Pro Arg Leu Leu Ala Ala Leu Cys Gly Ala Leu Leu Cys
 1               5                  10                  15

Ala Pro Ser Leu Leu Val Ala Leu Asp Asp Phe Cys Asp Ser Ser Leu
             20                  25                  30
```

-continued

```
Cys Leu Asn Gly Gly Thr Cys Leu Thr Gly Gln Asp Asn Asp Ile Tyr
            35                  40                  45
Cys Leu Cys Pro Glu Gly Phe Thr Gly Leu Val Cys Asn Glu Thr Glu
 50                  55                  60
Arg Gly Ile Cys Ser Lys Asn Pro Cys His Asn Gly Gly Leu Cys Glu
 65                  70                  75                  80
Glu Ile Ser Gln Glu Val Arg Gly Asp Val Phe Pro Ser Tyr Thr Cys
                    85                  90                  95
Thr Cys Leu Lys Gly Tyr Ala Gly Asn His Cys Glu Thr Glu Thr Asn
                100                 105                 110
Tyr Tyr Asn Leu Asp Gly Glu Tyr Met Phe Thr Thr Ala Val Pro Asn
                115                 120                 125
Thr Ala Val Pro Thr Pro Ala Pro Thr Pro Asp Leu Ser Asn Asn Leu
            130                 135                 140
Ala Ser Lys Cys Val Glu Pro Leu Gly Met Glu Asn Gly Asn Ile Ala
145                 150                 155                 160
Asn Ser Gln Ile Ala Ala Ser Ser Val Arg Val Thr Phe Leu Gly Leu
                165                 170                 175
Gln His Trp Val Pro Glu Leu Ala Arg Leu Asn Arg Ala Gly Met Val
            180                 185                 190
Asn Ala Trp Thr Pro Ser Ser Asn Asp Asp Asn Pro Trp Ile Gln Val
            195                 200                 205
Asn Leu Leu Arg Arg Met Trp Val Thr Gly Val Thr Gln Gly Ala
210                 215                 220
Ser Arg Leu Ala Ser His Glu Tyr Leu Lys Ala Phe Lys Val Ala Tyr
225                 230                 235                 240
Ser Leu Asn Gly His Glu Phe Asp Phe Ile His Asp Val Asn Lys Lys
                245                 250                 255
His Lys Glu Phe Val Gly Asn Trp Asn Lys Asn Ala Val His Val Asn
            260                 265                 270
Leu Phe Glu Thr Pro Val Glu Ala Gln Tyr Val Arg Leu Tyr Pro Thr
            275                 280                 285
Ser Cys His Thr Ala Cys Thr Leu Arg Phe Glu Leu Leu Gly Cys Glu
290                 295                 300
Leu Asn Gly Cys Ala Asn Pro Leu Gly Leu Lys Asn Asn Ser Ile Pro
305                 310                 315                 320
Asp Lys Gln Ile Thr Ala Ser Ser Tyr Lys Thr Trp Gly Leu His
                325                 330                 335
Leu Phe Ser Trp Asn Pro Ser Tyr Ala Arg Leu Asp Lys Gln Gly Asn
            340                 345                 350
Phe Asn Ala Trp Val Ala Gly Ser Tyr Gly Asn Asp Gln Trp Leu Gln
            355                 360                 365
Val Asp Leu Gly Ser Ser Lys Glu Val Thr Gly Ile Ile Thr Gln Gly
            370                 375                 380
Ala Arg Asn Phe Gly Ser Val Gln Phe Val Ala Ser Tyr Lys Val Ala
385                 390                 395                 400
Tyr Ser Asn Asp Ser Ala Asn Trp Thr Glu Tyr Gln Asp Pro Arg Thr
                405                 410                 415
Gly Ser Ser Lys Ile Phe Pro Gly Asn Trp Asp Asn His Ser His Lys
                420                 425                 430
Lys Asn Leu Phe Glu Thr Pro Ile Leu Ala Arg Tyr Val Arg Ile Leu
            435                 440                 445
```

```
Pro Val Ala Trp His Asn Arg Ile Ala Leu Arg Leu Glu Leu Leu Gly
    450                 455                 460

Cys
465
```

(2) INFORMATION FOR SEQ ID NO:9:

(i) SEQUENCE CHARACTERISTICS:
        (A) LENGTH: 463 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:9:

```
Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
                20                  25                  30

Cys Leu Asn Gly Gly Thr Cys Leu Thr Gly Gln Asp Asn Asp Ile Tyr
            35                  40                  45

Cys Leu Cys Pro Glu Gly Phe Thr Gly Leu Val Cys Asn Glu Thr Glu
50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
                100                 105                 110

Tyr Tyr Asn Leu Asp Gly Glu Tyr Met Phe Thr Thr Ala Val Pro Asn
            115                 120                 125

Thr Ala Val Pro Thr Pro Ala Pro Thr Pro Asp Leu Ser Asn Asn Leu
130                 135                 140

Ala Ser Arg Cys Ser Thr Gln Leu Gly Met Glu Gly Gly Ala Ile Ala
145                 150                 155                 160

Asp Ser Gln Ile Ser Ala Ser Tyr Val Tyr Met Gly Phe Met Gly Leu
                165                 170                 175

Gln Arg Trp Gly Pro Glu Leu Ala Arg Leu Tyr Arg Thr Gly Ile Val
            180                 185                 190

Asn Ala Trp His Ala Ser Asn Tyr Asp Ser Leu Pro Trp Ile Gln Val
            195                 200                 205

Asn Leu Leu Arg Lys Met Arg Val Ser Gly Val Met Thr Gln Gly Ala
    210                 215                 220

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
                245                 250                 255

Asp Lys Glu Phe Leu Gly Asn Leu Asp Asn Asn Ser Leu Lys Val Asn
                260                 265                 270

Met Phe Asn Pro Thr Leu Glu Ala Glu Tyr Ile Arg Leu Tyr Pro Val
            275                 280                 285

Ser Cys His Arg Gly Cys Thr Leu Arg Phe Glu Leu Leu Gly Cys Glu
290                 295                 300

Leu His Gly Cys Leu Glu Pro Leu Gly Leu Lys Asn Asn Thr Ile Pro
305                 310                 315                 320
```

-continued

```
Asp Ser Gln Met Ser Ala Ser Ser Tyr Lys Thr Trp Asn Leu Arg
            325                 330                 335

Ala Phe Gly Trp Tyr Pro His Leu Gly Arg Leu Asp Asn Gln Gly Lys
            340                 345                 350

Ile Asn Ala Trp Thr Ala Gln Ser Asn Ser Ala Lys Glu Trp Leu Gln
            355                 360                 365

Val Asp Leu Gly Thr Gln Arg Gln Val Thr Gly Ile Ile Thr Gln Gly
370                 375                 380

Ala Arg Asp Phe Gly His Ile Gln Tyr Val Glu Ser Tyr Lys Val Ala
385                 390                 395                 400

His Ser Asp Asp Gly Val Gln Trp Thr Val Tyr Glu Glu Gln Gly Ser
            405                 410                 415

Ser Lys Val Phe Gln Gly Asn Leu Asp Asn Asn Ser His Lys Lys Asn
            420                 425                 430

Ile Phe Glu Lys Pro Phe Met Ala Arg Lys Val Arg Val Leu Pro Val
            435                 440                 445

Ser Trp His Asn Arg Ile Thr Leu Arg Leu Glu Leu Leu Gly Cys
            450                 455                 460
```

(2) INFORMATION FOR SEQ ID NO:10:

(i) SEQUENCE CHARACTERISTICS:
        (A) LENGTH: 160 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:10:

```
Lys Cys Val Glu Pro Leu Gly Met Glu Asn Gly Asn Ile Ala Asn Ser
1               5                   10                  15

Gln Ile Ala Ala Ser Ser Val Arg Val Thr Phe Leu Gly Leu Gln His
            20                  25                  30

Trp Val Pro Glu Leu Ala Arg Leu Asn Arg Ala Gly Met Val Asn Ala
            35                  40                  45

Trp Thr Pro Ser Ser Asn Asp Asp Asn Pro Trp Ile Gln Val Asn Leu
50                  55                  60

Leu Arg Arg Met Trp Val Thr Gly Val Val Thr Gln Gly Ala Ser Arg
65                  70                  75                  80

Leu Ala Ser His Glu Tyr Leu Lys Ala Phe Lys Val Ala Tyr Ser Leu
            85                  90                  95

Asn Gly His Glu Phe Asp Phe Ile His Asp Val Asn Lys Lys His Lys
            100                 105                 110

Glu Phe Val Gly Asn Trp Asn Lys Asn Ala Val His Val Asn Leu Phe
            115                 120                 125

Glu Thr Pro Val Glu Ala Gln Tyr Val Arg Leu Tyr Pro Thr Ser Cys
            130                 135                 140

His Thr Ala Cys Thr Leu Arg Phe Glu Leu Leu Gly Cys Glu Leu Asn
145                 150                 155                 160
```

(2) INFORMATION FOR SEQ ID NO:11:

(i) SEQUENCE CHARACTERISTICS:
        (A) LENGTH: 160 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:11:

```
Arg Cys Ser Thr Gln Leu Gly Met Glu Gly Gly Ala Ile Ala Asp Ser
 1               5                  10                  15

Gln Ile Ser Ala Ser Tyr Val Tyr Met Gly Phe Met Gly Leu Gln Arg
            20                  25                  30

Trp Gly Pro Glu Leu Ala Arg Leu Tyr Arg Thr Gly Ile Val Asn Ala
        35                  40                  45

Trp His Ala Ser Asn Tyr Asp Ser Leu Pro Trp Ile Gln Val Asn Leu
    50                  55                  60

Leu Arg Lys Met Arg Val Ser Gly Val Met Thr Gln Gly Ala Ser Arg
65                  70                  75                  80

Ala Gly Arg Ala Glu Tyr Leu Lys Thr Phe Lys Val Ala Tyr Ser Leu
                85                  90                  95

Asp Gly Arg Lys Phe Glu Phe Ile Gln Asp Glu Ser Gly Gly Asp Lys
            100                 105                 110

Glu Phe Leu Gly Asn Leu Asp Asn Asn Ser Leu Lys Val Asn Met Phe
        115                 120                 125

Asn Pro Thr Leu Glu Ala Glu Tyr Ile Arg Leu Tyr Pro Val Ser Cys
    130                 135                 140

His Arg Gly Cys Thr Leu Arg Phe Glu Leu Leu Gly Cys Glu Leu His
145                 150                 155                 160
```

(2) INFORMATION FOR SEQ ID NO:12:

(i) SEQUENCE CHARACTERISTICS:
   (A) LENGTH: 159 amino acids
   (B) TYPE: amino acid
   (C) STRANDEDNESS: unknown
   (D) TOPOLOGY: unknown (ii) MOLECULE TYPE: peptide (xi) SEQUENCE DESCRIPTION: SEQ ID NO:12:

```
Gly Cys Ala Asn Pro Leu Gly Leu Lys Asn Asn Ser Ile Pro Asp Lys
 1               5                  10                  15

Gln Ile Thr Ala Ser Ser Ser Tyr Lys Thr Trp Gly Leu His Leu Phe
            20                  25                  30

Ser Trp Asn Pro Ser Tyr Ala Arg Leu Asp Lys Gln Gly Asn Phe Asn
        35                  40                  45

Ala Trp Val Ala Gly Ser Tyr Gly Asn Asp Gln Trp Leu Gln Val Asp
    50                  55                  60

Leu Gly Ser Ser Lys Glu Val Thr Gly Ile Ile Thr Gln Gly Ala Arg
65                  70                  75                  80

Asn Phe Gly Ser Val Gln Phe Val Ala Ser Tyr Lys Val Ala Tyr Ser
                85                  90                  95

Asn Asp Ser Ala Asn Trp Thr Glu Tyr Gln Asp Pro Arg Thr Gly Ser
            100                 105                 110

Ser Lys Ile Phe Pro Gly Asn Trp Asp Asn His Ser His Lys Lys Asn
        115                 120                 125

Leu Phe Glu Thr Pro Ile Leu Ala Arg Tyr Val Arg Ile Leu Pro Val
    130                 135                 140

Ala Trp His Asn Arg Ile Ala Leu Arg Leu Glu Leu Leu Gly Cys
145                 150                 155
```

(2) INFORMATION FOR SEQ ID NO:13:

(i) SEQUENCE CHARACTERISTICS:
        (A) LENGTH: 157 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:13:

Gly Cys Leu Glu Pro Leu Gly Leu Lys Asn Asn Thr Ile Pro Asp Ser
 1               5                  10                  15

Gln Met Ser Ala Ser Ser Ser Tyr Lys Thr Trp Asn Leu Arg Ala Phe
                20                  25                  30

Gly Trp Tyr Pro His Leu Gly Arg Leu Asp Asn Gln Gly Lys Ile Asn
            35                  40                  45

Ala Trp Thr Ala Gln Ser Asn Ser Ala Lys Glu Trp Leu Gln Val Asp
50                  55                  60

Leu Gly Thr Gln Arg Gln Val Thr Gly Ile Ile Thr Gln Gly Ala Arg
65                  70                  75                  80

Asp Phe Gly His Ile Gln Tyr Val Glu Ser Tyr Lys Val Ala His Ser
                85                  90                  95

Asp Asp Gly Val Gln Trp Thr Val Tyr Glu Glu Gln Gly Ser Ser Lys
            100                 105                 110

Val Phe Gln Gly Asn Leu Asp Asn Asn Ser His Lys Lys Asn Ile Phe
            115                 120                 125

Glu Lys Pro Phe Met Ala Arg Lys Val Arg Val Leu Pro Val Ser Trp
130                 135                 140

His Asn Arg Ile Thr Leu Arg Leu Glu Leu Leu Gly Cys
145                 150                 155

(2) INFORMATION FOR SEQ ID NO:14:

(i) SEQUENCE CHARACTERISTICS:
        (A) LENGTH: 160 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:14:

Gly Cys Ser Thr Pro Leu Gly Met Glu Asn Gly Lys Ile Glu Asn Lys
 1               5                  10                  15

Gln Ile Thr Ala Ser Ser Phe Lys Lys Ser Trp Trp Gly Asp Tyr Trp
                20                  25                  30

Glu Pro Phe Arg Ala Arg Leu Asn Ala Gln Gly Arg Val Asn Ala Trp
            35                  40                  45

Gln Ala Lys Ala Asn Asn Asn Lys Gln Trp Leu Glu Ile Asp Leu Leu
50                  55                  60

Lys Ile Lys Lys Ile Thr Ala Ile Ile Thr Gln Gly Cys Lys Ser Leu
65                  70                  75                  80

Ser Ser Glu Met Tyr Val Lys Ser Tyr Thr Ile His Tyr Ser Glu Gln
                85                  90                  95

Gly Val Glu Trp Lys Pro Tyr Arg Leu Lys Ser Ser Met Val Asp Lys
            100                 105                 110

Ile Phe Glu Gly Asn Thr Asn Thr Lys Gly His Val Lys Asn Phe Phe
            115                 120                 125

Asn Pro Pro Ile Ile Ser Arg Phe Ile Arg Val Ile Pro Lys Thr Trp
130                 135                 140

Asn Gln Ser Ile Thr Leu Arg Leu Glu Leu Phe Gly Cys Asp Ile Tyr
145                 150                 155                 160

(2) INFORMATION FOR SEQ ID NO:15:

(i) SEQUENCE CHARACTERISTICS:
        (A) LENGTH: 160 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:15:

Ser Cys Ser Met Pro Leu Gly Met Glu Ser Lys Ala Ile Ser Asp Ala
1               5                   10                  15

Gln Ile Thr Ala Ser Ser Tyr Phe Thr Asn Met Phe Ala Thr Trp Ser
                20                  25                  30

Pro Ser Lys Ala Arg Leu His Leu Gln Gly Arg Ser Asn Ala Trp Arg
            35                  40                  45

Pro Gln Val Asn Asn Pro Lys Glu Trp Leu Gln Val Asp Phe Gln Lys
50                  55                  60

Thr Met Lys Val Thr Gly Val Thr Thr Gln Gly Val Lys Ser Leu Leu
65                  70                  75                  80

Thr Ser Met Tyr Val Lys Glu Phe Leu Ile Ser Ser Ser Gln Asp Gly
                85                  90                  95

His Gln Trp Thr Leu Phe Phe Gln Asn Gly Lys Val Lys Val Phe Gln
                100                 105                 110

Gly Asn Gln Asp Ser Phe Thr Pro Val Val Asn Ser Leu Asp Pro Pro
            115                 120                 125

Leu Leu Thr Arg Tyr Leu Arg Ile His Pro Gln Ser Trp Val His Gln
130                 135                 140

Ile Ala Leu Arg Met Glu Val Leu Gly Cys Glu Ala Gln Asp Leu Tyr
145                 150                 155                 160

(2) INFORMATION FOR SEQ ID NO:16:

(i) SEQUENCE CHARACTERISTICS:
        (A) LENGTH: 159 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:16:

Asp Cys Arg Met Pro Met Gly Leu Ser Thr Gly Ile Ile Ser Asp Ser
1               5                   10                  15

Gln Ile Lys Ala Ser Glu Phe Leu Gly Tyr Trp Glu Pro Arg Leu Ala
                20                  25                  30

Arg Leu Asn Asn Gly Gly Ser Tyr Asn Ala Trp Ser Val Glu Lys Leu
            35                  40                  45

Ala Ala Glu Phe Ala Ser Lys Pro Trp Ile Gln Val Asp Met Gln Lys
50                  55                  60

Glu Val Ile Ile Thr Gly Ile Gln Thr Gln Gly Ala Lys His Tyr Leu
65                  70                  75                  80

Lys Ser Cys Tyr Thr Thr Glu Phe Tyr Val Ala Tyr Ser Ser Asn Gln
                85                  90                  95

Ile Asn Trp Gln Ile Phe Lys Gly Asn Ser Thr Arg Asn Val Met Tyr
                100                 105                 110

```
Phe Asn Gly Asn Ser Asp Ala Ser Thr Ile Lys Glu Asn Gln Phe Asp
            115                 120                 125

Pro Pro Ile Val Ala Arg Tyr Ile Arg Ile Ser Pro Thr Arg Ala Tyr
130                 135                 140

Asn Arg Pro Thr Leu Arg Leu Glu Leu Gln Gly Cys Glu Val Asn
145                 150                 155
```

(2) INFORMATION FOR SEQ ID NO:17:

(i) SEQUENCE CHARACTERISTICS:
        (A) LENGTH: 154 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:17:

```
Lys Cys Gln Thr Pro Leu Gly Met Ala Ser Gly His Ile Arg Asp Phe
1                   5                   10                  15

Gln Ile Thr Ala Ser Gly Gln Tyr Gly Gln Trp Ala Pro Lys Leu Ala
                20                  25                  30

Arg Leu His Tyr Ser Gly Ser Ile Asn Ala Trp Ser Thr Lys Glu Pro
            35                  40                  45

Phe Ser Trp Ile Lys Val Asp Leu Leu Ala Pro Met Ile Ile His Gly
50                  55                  60

Ile Lys Thr Gln Gly Ala Arg Gln Lys Phe Ser Ser Leu Tyr Ile Ser
65                  70                  75                  80

Gln Phe Ile Ile Met Tyr Ser Leu Asp Gly Lys Lys Trp Gln Thr Tyr
                85                  90                  95

Arg Gly Asn Ser Thr Gly Thr Leu Met Val Phe Phe Gly Asn Val Asp
                100                 105                 110

Ser Ser Gly Ile Lys His Asn Ile Phe Asn Pro Pro Ile Ile Ala Arg
            115                 120                 125

Tyr Ile Arg Leu His Pro Thr His Tyr Ser Ile Arg Ser Thr Leu Arg
130                 135                 140

Met Glu Leu Met Gly Cys Asp Leu Asn Ser
145                 150
```

(2) INFORMATION FOR SEQ ID NO:18:

(i) SEQUENCE CHARACTERISTICS:
        (A) LENGTH: 156 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:18:

```
Gln Cys Lys Glu Ala Leu Gly Met Glu Ser Gly Glu Ile His Phe Asp
1                   5                   10                  15

Gln Ile Ser Val Ser Ser Gln Tyr Ser Met Asn Trp Ser Ala Glu Arg
                20                  25                  30

Ser Arg Leu Asn Tyr Val Glu Asn Gly Trp Thr Pro Gly Glu Asp Thr
            35                  40                  45

Val Lys Glu Trp Ile Gln Val Asp Leu Glu Asn Leu Arg Phe Val Ser
50                  55                  60

Gly Ile Gly Tyr Gln Gly Ala Ile Ser Lys Glu Thr Lys Lys Lys Tyr
65                  70                  75                  80
```

```
Phe Val Lys Ser Tyr Lys Val Asp Ile Ser Ser Asn Gly Glu Asp Trp
                85                  90                  95

Ile Thr Leu Lys Asp Gly Asn Lys His Leu Val Phe Thr Gly Asn Thr
            100                 105                 110

Asp Ala Thr Asp Val Val Tyr Arg Pro Phe Ser Lys Pro Val Ile Thr
            115                 120                 125

Arg Phe Val Arg Leu Arg Pro Val Thr Trp Glu Asn Gly Ile Ser Leu
    130                 135                 140

Arg Phe Glu Leu Tyr Gly Cys Lys Ile Thr Asp Tyr
145                 150                 155
```

(2) INFORMATION FOR SEQ ID NO:19:

(i) SEQUENCE CHARACTERISTICS:
       (A) LENGTH: 161 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:19:

```
Pro Cys Ser Arg Met Leu Gly Met Val Ser Gly Leu Ile Ser Asp Ser
1               5                   10                  15

Gln Ile Thr Ala Ser Ser Gln Val Asp Arg Asn Trp Val Pro Glu Leu
            20                  25                  30

Ala Arg Leu Val Thr Ser Arg Ser Gly Trp Ala Leu Pro Pro Ser Asn
        35                  40                  45

Thr His Pro Tyr Thr Lys Glu Trp Leu Gln Ile Asp Leu Ala Glu Glu
    50                  55                  60

Lys Ile Val Arg Gly Val Ile Ile Gln Gly Gly Lys His Lys Glu Asn
65              70                  75                  80

Lys Val Phe Met Arg Lys Phe Lys Ile Gly Tyr Ser Asn Asn Gly Thr
                85                  90                  95

Glu Trp Glu Met Ile Met Asp Ser Ser Lys Asn Lys Pro Lys Thr Phe
            100                 105                 110

Glu Gly Asn Thr Asn Tyr Asp Thr Pro Glu Leu Arg Thr Phe Ala His
            115                 120                 125

Ile Thr Thr Gly Phe Ile Arg Ile Ile Pro Glu Arg Ala Ser Ala Ser
    130                 135                 140

Gly Leu Ala Leu Arg Leu Glu Leu Leu Gly Cys Glu Val Glu Thr Pro
145                 150                 155                 160

Thr
```

(2) INFORMATION FOR SEQ ID NO:20:

(i) SEQUENCE CHARACTERISTICS:
       (A) LENGTH: 156 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:20:

```
Lys Cys Arg Tyr Ala Leu Gly Met Gln Asp Arg Thr Ile Pro Asp Ser
1               5                   10                  15

Asp Ile Ser Ala Ser Ser Ser Trp Ser Asp Ser Thr Ala Ala Arg His
            20                  25                  30
```

```
Ser Arg Leu Glu Ser Ser Asp Gly Asp Gly Ala Trp Cys Pro Ala Gly
        35                  40                  45
Ser Val Phe Pro Lys Glu Glu Glu Tyr Leu Gln Val Asp Leu Gln Arg
 50                  55                  60
Leu His Leu Val Ala Leu Val Gly Thr Gln Arg His Ala Gly Gly
 65                  70                  75                  80
Leu Gly Lys Glu Phe Ser Arg Ser Tyr Arg Leu Arg Tyr Ser Arg Asp
                85                  90                  95
Gly Arg Arg Trp Met Gly Trp Lys Asp Arg Trp Gly Gln Glu Val Ile
                100                 105                 110
Ser Gly Asn Glu Asp Pro Glu Gly Val Val Leu Lys Asp Leu Gly Pro
                115                 120                 125
Pro Met Val Ala Arg Leu Val Arg Phe Tyr Pro Arg Ala Asp Arg Val
            130                 135                 140
Met Ser Val Cys Leu Arg Val Glu Leu Tyr Gly Cys
 145                 150                 155
```

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:21:

```
Gly Cys Leu Glu Pro Leu
 1               5
```

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:22:

```
Trp Gly Pro Glu Leu Ala Arg
 1               5
```

(2) INFORMATION FOR SEQ ID NO:23:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:23:

```
Trp Ala Pro Glu Leu Ala Arg
 1               5
```

(2) INFORMATION FOR SEQ ID NO:24:

(i) SEQUENCE CHARACTERISTICS:
        (A) LENGTH: 14 amino acids
        (B) TYPE: amino acid (C) STRANDEDNESS: unknown
        (D) TOPOLOGY: unknown (ii) MOLECULE TYPE: peptide (xi) SEQUENCE DESCRIPTION: SEQ ID NO:24:

Lys Met Xaa Val Thr Xaa Val Val Thr Gln Gly Ala Ser Arg
1               5                   10

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:25:

Leu Asn Met Phe Ser Ala Pro Leu Glu Val Gln Tyr Val Arg
1               5                   10

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:26:

Ile Asn Leu Phe Asp Thr Pro Leu Glu Thr Gln Tyr Val Arg
1               5                   10

(2) INFORMATION FOR SEQ ID NO:27:

(i) SEQUENCE CHARACTERISTICS:
        (A) LENGTH: 108 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:27:

Asp Gly Ser Glu Ala Trp Cys Ser Ser Ile Val Asp Thr Asn Gln Tyr
1               5                   10                  15

Ile Val Ala Gly Cys Glu Val Pro Arg Thr Phe Met Cys Val Ala Leu
            20                  25                  30

Gln Gly Arg Gly Asp Ala Asp Gln Trp Val Thr Ser Tyr Lys Ile Arg
            35                  40                  45

Tyr Ser Leu Asp Asn Val Ser Trp Phe Glu Tyr Arg Asn Gly Ala Ala
    50                  55                  60

Val Thr Gly Val Thr Asp Arg Asn Thr Val Val Asn His Phe Phe Asp
65                  70                  75                  80

Thr Pro Ile Arg Ala Arg Ser Ile Ala Ile His Pro Leu Thr Trp Asn
                85                  90                  95

Gly His Ile Ser Leu Arg Cys Glu Phe Tyr Thr Gln
                100                 105

(2) INFORMATION FOR SEQ ID NO:28:

(i) SEQUENCE CHARACTERISTICS:

-continued

```
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:28:

Phe Glu Leu Leu Gly Cys Glu Leu Asn Gly Cys Leu Glu Pro Leu
1               5                   10                  15

(2) INFORMATION FOR SEQ ID NO:29:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:29:

Val Glu Leu Leu Gly Cys
1               5
```